(12) United States Patent
Sadikali et al.

(10) Patent No.: US 7,634,733 B2
(45) Date of Patent: Dec. 15, 2009

(54) IMAGING HISTORY DISPLAY SYSTEM AND METHOD

(75) Inventors: Navid H. Sadikali, Kitchener (CA); Gavin A. Rough, Waterloo (CA); Robin M. Dube, New Hamburg (CA)

(73) Assignee: Agfa Inc., Toronto (CA)

( * ) Notice: Subject to any disclaimer, the term of this patent is extended or adjusted under 35 U.S.C. 154(b) by 356 days.

(21) Appl. No.: 11/522,364

(22) Filed: Sep. 18, 2006

(65) Prior Publication Data

US 2008/0126982 A1 May 29, 2008

(51) Int. Cl.
G06F 13/00 (2006.01)
G06F 15/00 (2006.01)
(52) U.S. Cl. .................................. 715/738; 715/853
(58) Field of Classification Search .............. 715/700, 715/760, 738, 740, 837–839, 850–853
See application file for complete search history.

(56) References Cited

U.S. PATENT DOCUMENTS 6,734,880 B2 * 5/2004 Chang et al. ............... 715/738
7,058,901 B1 6/2006 Hafey et al.
2005/0259116 A1 * 11/2005 Araoka ...................... 345/619

OTHER PUBLICATIONS

PCT Search Report/Written Opinion mailed on Feb. 26, 2008.

* cited by examiner

*Primary Examiner*—Kevin Nguyen
(74) *Attorney, Agent, or Firm*—Bereskin & Parr; Isis E. Caulder

(57) ABSTRACT

An imaging history display system and method is disclosed comprising diagnostic and patient summary interfaces for displaying, comparing and managing medical images. Imaging history display system displays studies in two interface modes in response to commands received from a user workstation. Display entities are displayed on display areas within display entity boxes that are defined by display entity layouts. Contextual summaries of display entities are provided in the patient summary interface to facilitate accurate and exhaustive diagnoses. Contextual summaries are generated in part based on pre-determined relevancy information. Display entities are easily organized in the patient summary interface. Display entities are easily activated in the diagnostic interface for diagnostic and comparison purposes.

32 Claims, 24 Drawing Sheets

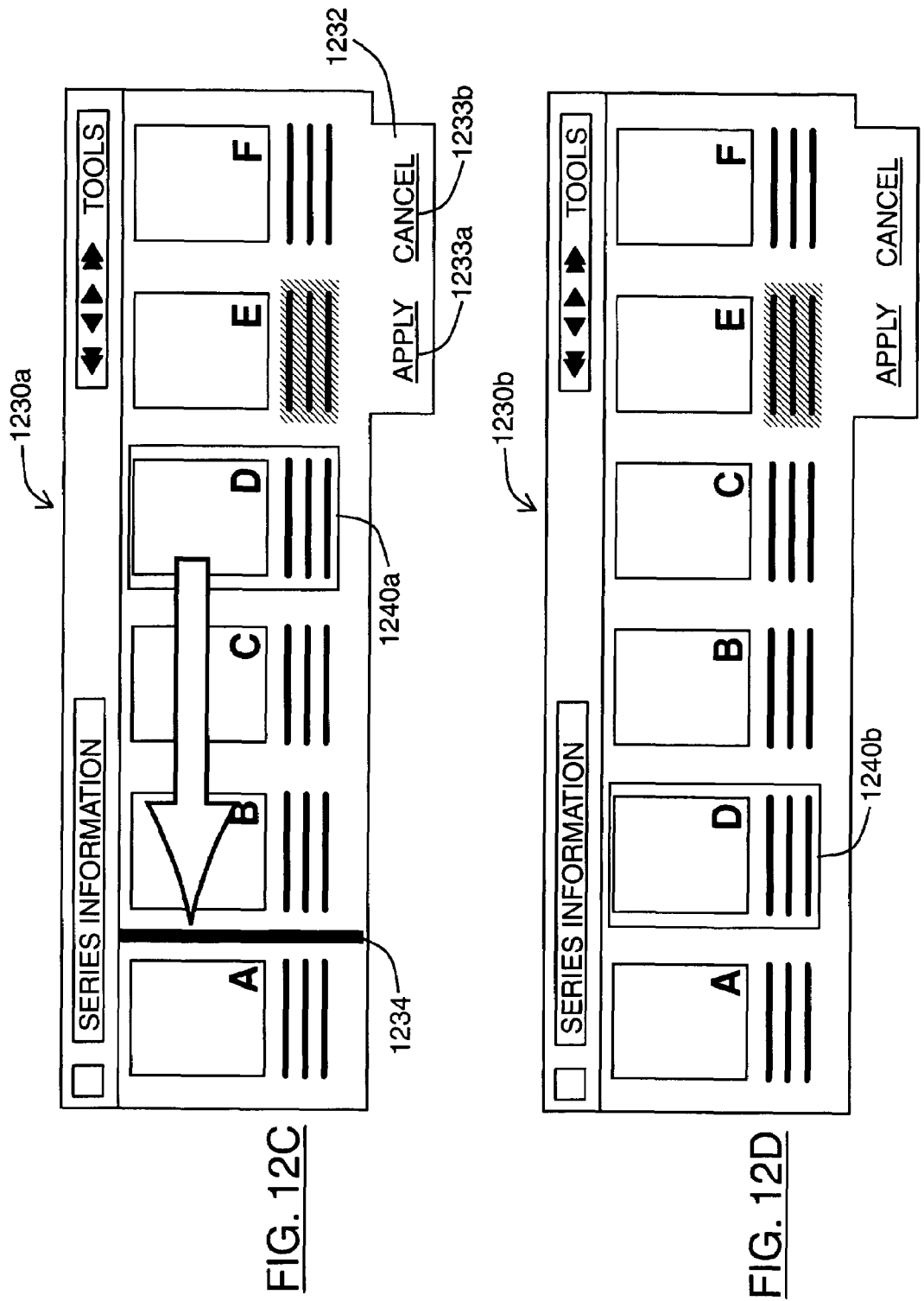

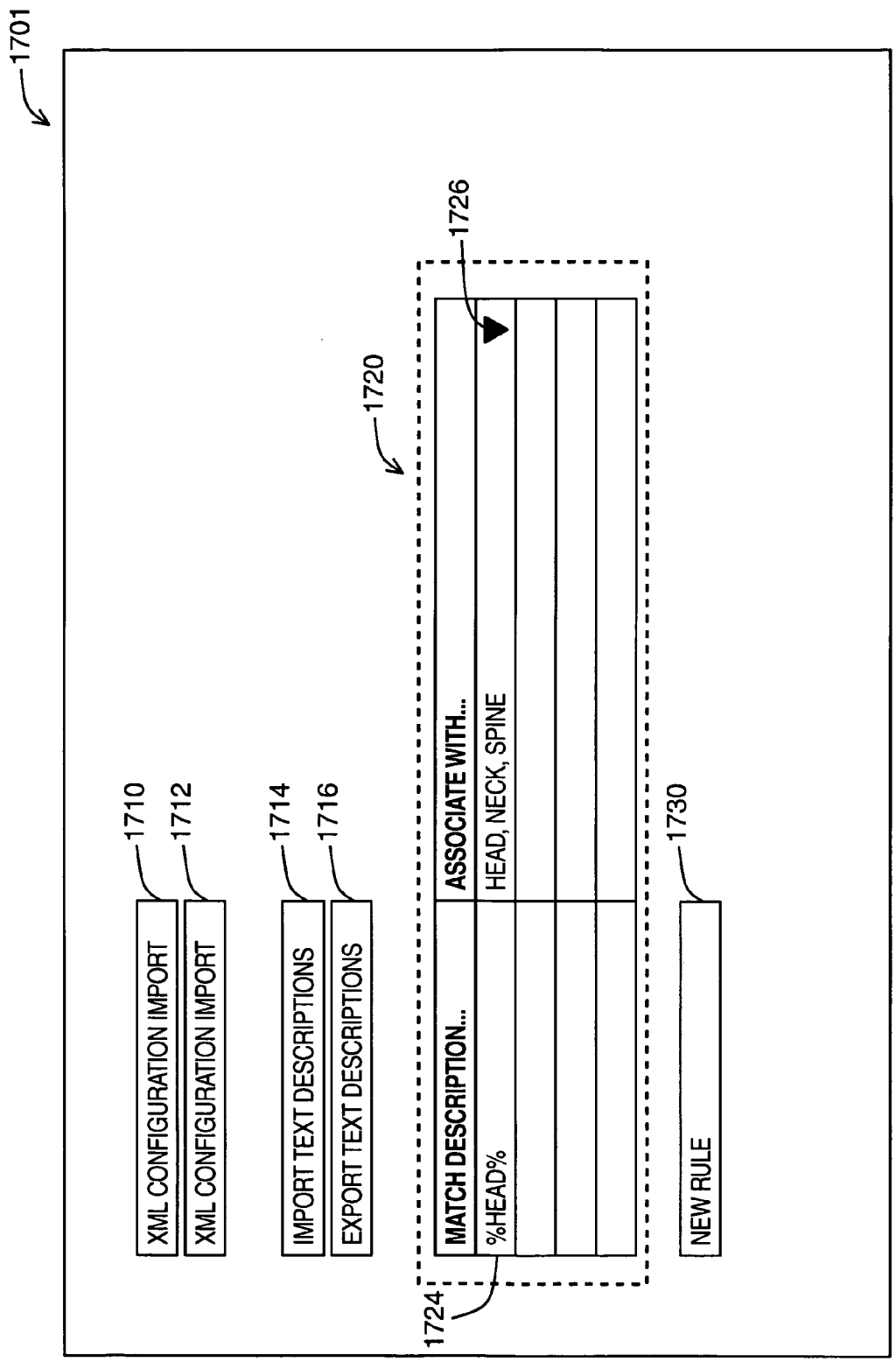

IMAGING HISTORY DISPLAY SYSTEM AND METHOD

FIELD

The embodiments described herein relate to an image viewing system and method and more particularly to a system and method for viewing and organizing medical diagnostic imaging studies on a contextual basis.

BACKGROUND

Commercially available image display systems in the medical field utilize various techniques to present image data to a user. Specifically, image data produced within modalities such as Computed Tomography (CT), Magnetic Resonance (MR) and the like is displayed on a display terminal for review by a medical practitioner at a medical treatment site. This image data is used by the medical practitioner to determine the presence or absence of a disease, tissue damage, etc. Through visual comparisons with prior imaging studies, medical practitioners are able to make or improve diagnoses based on changes in a patient's imaging studies over time.

Currently, large volume imaging studies utilized by medical treatment sites, such as CT and MR, pose a significant diagnostic problem due to the large number of image data files that are created and stored for later review. A typical image dataset may easily contain over 2000 slices that translate into a similar number of image data files organized into multiple series. Further, Picture Archiving and Communication Systems (PACS) utilized by medical treatment sites have the ability to present image datasets from multiple modalities, spanning several years. Although the availability of imaging studies from multiple modalities is of benefit to medical practitioners, it is difficult to isolate only relevant prior studies. Further, the amount of data available requires that medical practitioners engage in a time-intensive exercise to filter through studies, series and images, to identify only those that are most relevant to the current diagnosis.

This filtering process is difficult, making an exhaustive comparison of current medical images with a patient's prior history impractical. Moreover, image data is often presented by date. However, medical practitioners are less interested in exact dates than in time periods, for example, the previous quarter or year.

SUMMARY

The embodiments described herein provide in one aspect, a method for displaying a first image on a diagnostic interface, wherein the method comprises:

(a) providing a thumbnail representation of the first image at a point of origin on a patient summary interface positioned over the diagnostic interface such that the patient summary interface at least in part obscures the patient summary interface;

(b) determining whether the thumbnail representation has been selected and is being dragged on the patient summary interface from the point of origin;

(c) if (b) is true, then reducing the opacity of the patient summary interface such that the first image is no longer obscured by the patient summary interface;

(d) receiving a user command to display the first image on the diagnostic interface and causing the first image to be displayed on the diagnostic interface; and (e) increasing the opacity of the patient summary interface such that the first image is again at least in part obscured by the patient summary interface.

The embodiments described herein provide in another aspect, a system for displaying a first image on a diagnostic interface, wherein the system comprises:

(a) a memory for storing the first image;

(b) a processor coupled to the memory for:

(A) providing a thumbnail representation of the first image at a point of origin on a patient summary interface positioned over the diagnostic interface such that the patient summary interface at least in part obscures the patient summary interface;

(B) determining whether the thumbnail representation has been selected and is being dragged on the patient summary interface from the point of origin;

(C) determining if (B) is true, and if so then reducing the opacity of the patient summary interface such that the first image is no longer obscured by the patient summary interface;

(D) receiving a user command to display the first image on the diagnostic interface and causing the first image to be displayed on the diagnostic interface; and (E) increasing the opacity of the patient summary interface such that the first image is again at least in part obscured by the patient summary interface.

The embodiments described herein provide in another aspect, a method of providing a contextual historical summary display within a viewable area on a patient summary interface for a plurality of images wherein each image is associated with a time period and adapted to be displayed on a diagnostic interface, said method comprising:

(a) associating a representative icon with each image;

(b) initially grouping one or more representative icons together according to time period;

(c) determining whether all of the representative icons can be displayed within the viewable area;

(d) if (c) is true then displaying the representative icons within the viewable area according to the grouping in (b); and (e) if (c) is false then further grouping one or more representative icons according to time period and displaying the representative icons within the viewable area.

The embodiments described herein provide in another aspect, a system for providing a contextual historical summary display within a viewable area on a patient summary interface for a plurality of images wherein each image is associated with a time period and adapted to be displayed on a diagnostic interface, said system comprising:

(a) a memory for storing the plurality of images; and (b) a processor coupled to the memory for:

(A) associating a representative icon with each image;

(B) initially grouping one or more representative icons together according to time period;

(C) determining whether all of the representative icons can be displayed within the viewable area;

(D) determining if (C) is true, and if so then displaying the representative icons within the viewable area according to the grouping in (B); and (E) determining if (C) is false, and if so then further grouping one or more representative icons according to time period and displaying the representative icons within the viewable area.

The embodiments described herein provide in another aspect, a method of associating a patient summary interface having a first and second element with a screen edge of a diagnostic interface, said method comprising:

(a) activating the first and second elements of the patient summary interface for display and displaying the active first and second elements of the patient summary interface;

(b) receiving a user command to associate the patient summary interface with a screen edge of the diagnostic interface;

(c) condensing the patient summary interface so that only the active first element is activated for display; and (d) displaying the active first element of condensed patient summary interface along the screen edge of said diagnostic interface.

The embodiments described herein provide in another aspect, a system for associating a patient summary interface having a first and second element with a screen edge of a diagnostic interface, said system comprising:

(a) a memory for storing the patient summary interface; and (b) a processor coupled to the memory for:

(A) activating the first and second elements of the patient summary interface for display and displaying the active first and second elements of the patient summary interface;

(B) receiving a user command to associate the patient summary interface with a screen edge of the diagnostic interface;

(C) condensing the patient summary interface so that only the active first element is activated for display; and (D) displaying the active first element of condensed patient summary interface along the screen edge of said diagnostic interface.

The embodiments described herein provide in another aspect, a method of dynamically adjusting the size of display entities having a graphic element and a textual element within a patient summary interface, said method comprising:

(a) receiving a user command;

(b) resizing the graphic element for each display entity in response to said user command; and (c) adjusting the textual element for each display entity in response to said user command.

The embodiments described herein provide in another aspect, a system for dynamically adjusting the size of display entities having a graphic element and a textual element within a patient summary interface, said system comprising:

(a) a memory for storing the display entities;

(b) a processor coupled to the memory for:

(A) receiving a user command;

(B) resizing the graphic element for each display entity in response to said user command; and (C) adjusting the textual element for each display entity in response to said user command.

The embodiments described herein provide in another aspect, a method of displaying a first representative image in association with a first image and displaying a second representative image in association with a second image, said method comprising:

(a) displaying the first representative image adjacent to the first image and the second representative image adjacent to the second image;

(b) delineating the first representative image from the second representative image using an interactive user interface element; and (c) hiding the first representative image if the interactive user element is selected.

The embodiments described herein provide in another aspect, a system for displaying a first representative image in association with a first image and displaying a second representative image in association with a second image, said system comprising:

(a) a memory for storing the first and second representative images; and (b) a processor coupled to the memory for:

(A) displaying the first representative image adjacent to the first image and the second representative image adjacent to the second image;

(B) delineating the first representative image from the second representative image using an interactive user interface element; and (C) hiding the first representative image if the interactive user element is selected.

The embodiments described herein provide in another aspect, a method of associating a first image associated with a first anatomic region with a second image associated with a second anatomic region, said method comprising:

(a) defining an anatomical relevancy rule that maps the first anatomic region to at least one anatomic region including the second anatomic region;

(b) applying the anatomical relevancy rule to the first image to determine whether the first anatomic region is mapped to the second anatomic region; and (c) if (b) is true then associating the first image with the second image.

The embodiments described herein provide in another aspect, a system for associating a first image associated with a first anatomic region with a second image associated with a second anatomic region, said system comprising:

(a) a memory for storing the first and second images;

(b) a processor coupled to the memory for:

(A) defining an anatomical relevancy rule that maps the first anatomic region to at least one anatomic region including the second anatomic region;

(B) applying the anatomical relevancy rule to the first image to determine whether the first anatomic region is mapped to the second anatomic region; and (C) determining if (B) is true, and if so then associating the first image with the second image.

Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which:

FIGS. 12C and 12D are schematic diagrams illustrating a method for changing the arrangement of image dataset series in the image dataset series management tool of FIG. 3;

FIGS. 17A and 17B are schematic diagrams of the relevancy mapping interface generated by the relevancy module.

Figure 1:
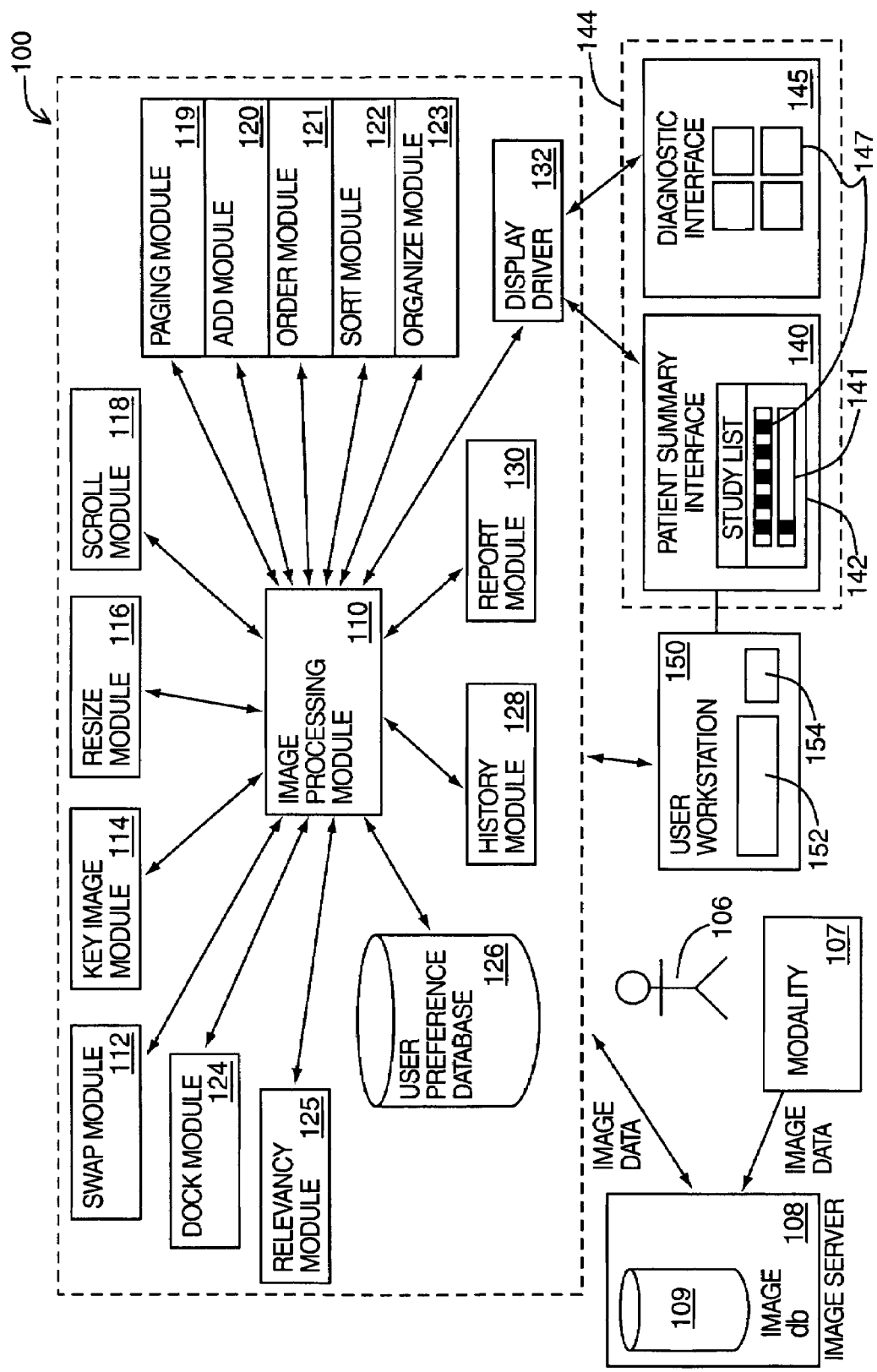
FIG. 1 is a block diagram of an imaging history display system.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, optionally, these embodiments are implemented in computer programs executing on programmable computers each comprising at least one processor, a data storage system (including volatile and non-volatile memory and/or storage elements), at least one input device, and at least one output device. For example and without limitation, the programmable computers may be a personal computer, laptop, personal data assistant, and cellular telephone. Program code is applied to input data to perform the functions described herein and generate output information. The output information is applied to one or more output devices, in known fashion.

Each program is optionally implemented in a high level procedural or object oriented programming and/or scripting language to communicate with a computer system. However, the programs can be implemented in assembly or machine language, if desired. In any case, the language may be a compiled or interpreted language. Each such computer program is optionally stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Reference is first made to FIG. 1, which is a block diagram illustrating an exemplary embodiment of an imaging history display system 100. Imaging history display system 100 is controlled by a medical practitioner user 106 via a user workstation 150 and is adapted to perform processing functions on one or more display entities 147 obtained from an image server 108. Display entities 147 may take various forms including complete medical imaging studies, distinct image series within a study or individual images. In addition, it should be understood that one or more studies, series or images are typically associated with a particular patient.

Imaging history display system 100 creates a list of imaging studies 143, each imaging study 143 containing one or more imaging series 141. The list of imaging studies 143 is displayed on a patient summary interface 140. Imaging history display system 100 further displays studies 141 for the patient whose study or studies are currently displayed on a diagnostic interface 145 on a user workstation 150, through a display driver 132, in response to commands issued by user 106. In the result, both patient summary interface 140 and diagnostic interface 145 are seen by user 106 via a user workstation 150. Imaging history display system 100 works contextually and dynamically to allow user 106 to manipulate user interface elements, such as icons representing studies 141, using user workstation 150, and therefore arrange said elements on-screen in a manner conducive to accurate and thorough medical diagnosis.

User workstation 150 contains a monitor 152 and an input device 154, and can be any number of devices including but not limited to a personal computer, laptop, medical imaging device terminal, cell phone, and personal data assistant (PDA). Imaging history display system 100 is used to provide image display formatting depending on user input through user workstation 150. Imaging history display system 100 is installed either on the non-volatile memory of user workstation 150 and/or on a central image server 108 such that user workstation 150 works with image server 108 in a client-server configuration.

Diagnostic interface 145 is optimized to provide high-resolution image display of display entities 147 (e.g. from studies 141) to user 106. Diagnostic interface 145 may display one or more display entities 147. Diagnostic interface 145 is optionally viewed on medical imaging quality display monitors with relatively high resolution typically used for viewing CT and MR studies (e.g. black and white "reading" monitors with a resolution of 1280×1024 and up).

Patient summary interface 140 is optimized for the review, gross comparison and organization of imaging studies 141 and therefore provides a user with, among other things, a study list 142. Patient summary interface 140 may not be displayed initially, and is invoked by user 106 when functions of the interface are required. Thereafter, patient summary interface 140 may also be dismissed by user 106 to provide maximal viewing area for display entities 147 on diagnostic interface 145.

Study list 142 provides a combined graphical and textual format listing of display entities 147 (e.g. studies 141) that are available for display. Study list 142 also includes associated identifying indicia (e.g. body part, modality, etc.) and organizes studies 141 in current and prior study categories. Typically, user 106 will review study list 142 and select listed studies 141. User 106 may select a study 141 and perform various operations using imaging history display system 100, including displaying the selected study 141 on diagnostic interface 145. Other associated textual information (e.g. patient information, image resolution quality, date of image capture, etc.) is simultaneously displayed within study list 142 to assist the user 106 in selection of studies 141. Patient summary interface 140 is optionally implemented as a graphical user interface window overlaying diagnostic interface 145.

It should be understood that many other types of display configurations could be utilized within imaging history display system 100 including the use of one, two or more displays.

Display entities 147 are obtained from image data generated by a modality 107, which is stored in an image database 109 on image server 108, where it may be retrieved by imaging history display system 100 for further processing. Modality 107 is any conventional image data generating device (e.g. computed radiography (CR) systems, computed tomography (CT) scanners, magnetic resonance imaging (MRI) systems, positron emission tomography (PET), ultrasound systems, etc.) utilized to generate image data that corresponds to patient medical exams. The image data generated by modality 107 is then utilized for making a diagnosis (e.g. for investigating the presence or absence of a diseased part or an injury or for ascertaining the characteristics of the diseased part or the injury). Modalities 107 may be positioned in a single location or facility, such as a medical facility, or may be remote from one another.

Imaging history display system 100 includes of a main image processing module 110 which coordinates the activities of a viewer swap module 112, a key image module 114, a resize module 116, a scroll module 118, a paging module 119, an add module 120, an order module 121, a sort module 122, an organize module 123, a dock module 124, a relevancy module 125, a history module 128 and a report module 130 in response to user commands sent by user 106 from user workstation 150 and stored user display preferences from a user preference database 126. Display driver 132 further generates patient summary interface 140, containing imaging study list 142, and diagnostic interface 145 for viewing images, containing display entities 147. Specifically, image processing module 110 is adapted to receive a request from user workstation 150 that indicates that particular display entities 147 (e.g., studies 141 or series 142, etc.) being displayed on the interfaces 140 and 145 are to be displayed in a reformatted manner selected to improve the usability of the overall medical imaging system. The various types of image display formatting and display options provided will be discussed.

Paging module 119 generates contextual toolbar 315 (FIG. 12A) for display in patient summary interface 140 for any medical imaging study view 250 that is linked with display entities 147 currently opened in diagnostic interface 145. The contextual toolbar 315 contains user interface elements to enable user 106 to incrementally view each display entity 147 within the current medical imaging study view 250 in detail on diagnostic interface 145.

Swap module 112 is utilized by image processing module 110 to provide user 106 with image swapping functionality between non-diagnostic and diagnostic interfaces 140 and 145. Swap module 112 allows user 106 to directly modify the actively viewed display entity 147 within diagnostic interface 145 by dragging a desired thumbnail over an unwanted display entity 147. This results in the unwanted display entity 147 being supplanted with a desired display entity 147 and thus occupying the display area previously executed by unwanted display entity 147. Swap module 112 will be discussed in more detail in respect of FIGS. 4A, 4B, 4C, 4D and 5 below.

Key image module 114 allows the user 106 to select specific display entities 147 for display as "key" images. "Key" images are displayed in a preferred position when arranged in series in studies 141. Key image module 114 allows user 106 to quickly identify important display entities 147 when viewing a study 141, because highlighted display entities 147 will have been previously identified as important by the current user 106 or by other users 106 with similar expertise. Key module 114 will be discussed in more detail in respect of FIG. 16 below.

Resize module 116 is utilized by image processing module 110 to provide user 106 with resizing functionality within patient summary interface 140. Resize module 116 allows user 106 to dynamically grow and shrink all thumbnail representations of the series 141 for each study 143 displayed in the patient summary interface to make identification of relevant series 141 and studies 143 possible from a thumbnail image. Resize module 116 reduces the need for user 106 to specifically and individually resize studies 141 (i.e., reducing unnecessary user-interface interaction) and facilitates efficient identification of relevant studies 141. Resize module 116 will be discussed in more detail in respect of FIGS. 10A, 10B and 11 below.

Scroll module 118 is utilized by image processing module 110 to provide user 106 with paging functionality within patient summary interface 140. Scroll module 118 allows user 106 to scroll through a group of display entities 147 that occupy more than the viewable area of the patient summary interface 140 by identifying when the viewable area is full and enabling scroll bars to facilitate scrolling. Only vertical scroll bars are used. If the thumbnails of series 141 for a single study 143 do not fit horizontally in the patient summary interface 140, then the thumbnails are wrapped onto a second line so the user never has to scroll horizontally to see all series/images for a study. Also, the scrolling module supports the use of the mouse scroll wheel, normally the center scroll button on a standard mouse, to scroll vertically through the patient history summary interface.

Add module 120 is utilized by image processing module 110 to provide user 106 with organizational functionality within patient summary interface 140. Add module 120 allows user 106 to add one or more display entities 147 together such as imaging series 141 to another imaging series 141 to allow for improved grouping of display entities 147 and therefore better display and comparison of studies, series and images for diagnostic purposes.

Order module 121 is utilized by image processing module 110 to provide user 106 with organizational functionality within imaging studies 141 displayed within study lists 142 within patient summary interface 140. Order module 121 allows user 106 to rearrange the order of imaging series 141 within a specific study 143 to, for example, correct the order of imaging series 141 that are displayed out of chronological order. Such functionality is particularly desirable where modalities 107 predate digital imaging methods and studies 143 were digitized in a random order. Order module 121 allows user 106 to initiate an ordering mode, drag and drop imaging series 141 to the desired positions, terminate the ordering mode and thus effect permanent changes to the ordering of imaging series 141 for the future. Use of an ordering mode is desirable because ordering actions are performed infrequently by user 106, while drag and drop operations are performed more frequently in a different context.

Sort module 122 is utilized by image processing module 110 to provide user 106 with sorting functionality within imaging studies 141 displayed within study lists 142 within patient summary interface 140. Sort module 122 allows user 106 to sort imaging series 141 by attributes relevant to the current study 141, for example, slice position, MR echo time, acquisition time, etc. Sort module 122 allows user 106 to quickly effect a temporary change in the arrangement of imaging series 141 that is desirable for comparative purposes to facilitate medical diagnosis.

Organize module 123 is utilized by image processing module 110 to provide user 106 with organizational functionality within patient summary interface 140. Organize module 123 allows the user 106 to add, duplicate, combine or split display imaging series 141 to allow for improved grouping of imaging series 141 and therefore better display and comparison of images for diagnostic purposes.

Dock module 124 is utilized by image processing module 110 to provide user 106 with docking functionality for patient summary interface 140 within diagnostic interface 145. Dock module 124 allows user 106 to position primary elements of patient summary interface 140 along an edge of diagnostic interface 145 while hiding secondary elements and providing maximal viewing area for display entity 147 displayed on diagnostic interface 145. Dock module 124 facilitates a drag and drop operation on the primary elements of patient summary interface 140 by the user 106 to position them on one of the vertical or horizontal edges of diagnostic interface 145 and determines an appropriate arrangement of interface elements as will be described in respect of FIGS. 8A, 8B, 8C, 9A and 9B below.

Relevancy module 125 is utilized by image processing module 110 to facilitate automated identification of relevant prior imaging studies, based on a plurality of rules. Image database 109 may contain a very large number of imaging studies 143 for each patient, which may not be relevant for the current user 106. Relevancy module 125 provides a means to filter irrelevant data from display, by mapping procedures and modalities to uniform, macro-anatomic regions. For example, an ultrasound of the kidney is mapped to the "abdomen" macro-anatomic region. Cross-anatomic studies, such as a body CT, which cover several macro-anatomic regions are associated with each of the regions the study covers, to ensure that no data is overlooked by user 106. User confidence in the relevancy mappings is paramount and it is important that each user 106 understand how relevancy is mapped. Further, the user can then map macro-anatomic regions to related macro-anatomic regions. For example, all "abdomen" studies can be mapped to other "abdomen" studies, along with "chest" studies and "pelvic" studies so that all studies for relevant body parts will be covered. The operation of relevancy module 125 is described in greater detail below, with respect to FIGS. 17A and 17B.

History module 128 is utilized by image processing module 110 to provide user 106 with historical summary functionality within patient summary interface 140. History module 128 allows user 106 to quickly identify imaging studies 141 available in the current patient summary interface 140 by generating an iconic summary of imaging studies 141 and arranging them in a compact, reverse chronological fashion such that more relevant imaging studies 141 are easily identifiable. The layout function uses an arrangement protocol to optionally condense the display of older imaging studies 141 and allow the display of newer imaging studies 141 in as much detail as possible. History module 128 will be discussed in more detail in respect of FIGS. 6 and 7 below.

Report module 130 is utilized by image processing module 110 to provide user 106 with display functionality for patient summary interface. Report module 130 allows user 106 to view clinical reports related to imaging studies 141 to facilitate the identification of "normal" or "abnormal" studies 141. The reports can be displayed in three ways. After clicking on a reports link, the entire imaging history summary interface 240 can replace all of the thumbnail images for each study with the report. So, each study that has a report will display that report, while studies that do not have reports can still display their thumbnail images of series. Alternately, the user can display the report for just one study by clicking on a report link within the study box. The report link only appears when a study has a dictated and/or approved report. The report can either replace the thumbnail images of series in the study slot, or be displayed in a pop-up window over the interface. The user can then close the pop-up when done reading the report.

It should be understood that in respect of the various functional modules discussed above, the user is using the thumbnail versions of the imaging series 141 in the imaging history summary interface 240 to make the discussed changes to the interface display.

Display driver 132 is a conventional display screen driver implemented using commercially available hardware and software. Display driver 132 ensures that various display entities 147 (e.g. studies, series, images, etc.) are displayed in a proper format within display interfaces 140 and 145 using an appropriate layout (e.g. study layout, series layout, image layout, etc.) on the user workstation 150.

While the functionality of the imaging history display system 100 will be discussed in relation to the display and arrangement of studies 141 within study lists 142 in interfaces 140 and 145, it should be understood that the functionality of imaging history display system 100 is equally applicable to the display and arrangement of any other display entity 147 within a prescribed display area. More generally, it should be understood that the functionality of the swap module 112, key image module 114, resize module 116, scroll module 118, paging module 119, add module 120, order module 121, sort module 122, organize module 123, dock module 124, relevancy module 125, history module 128 and report module 130 can be applied to any form of display system that is used to display entities 147 to a user 106.

Figure 2:
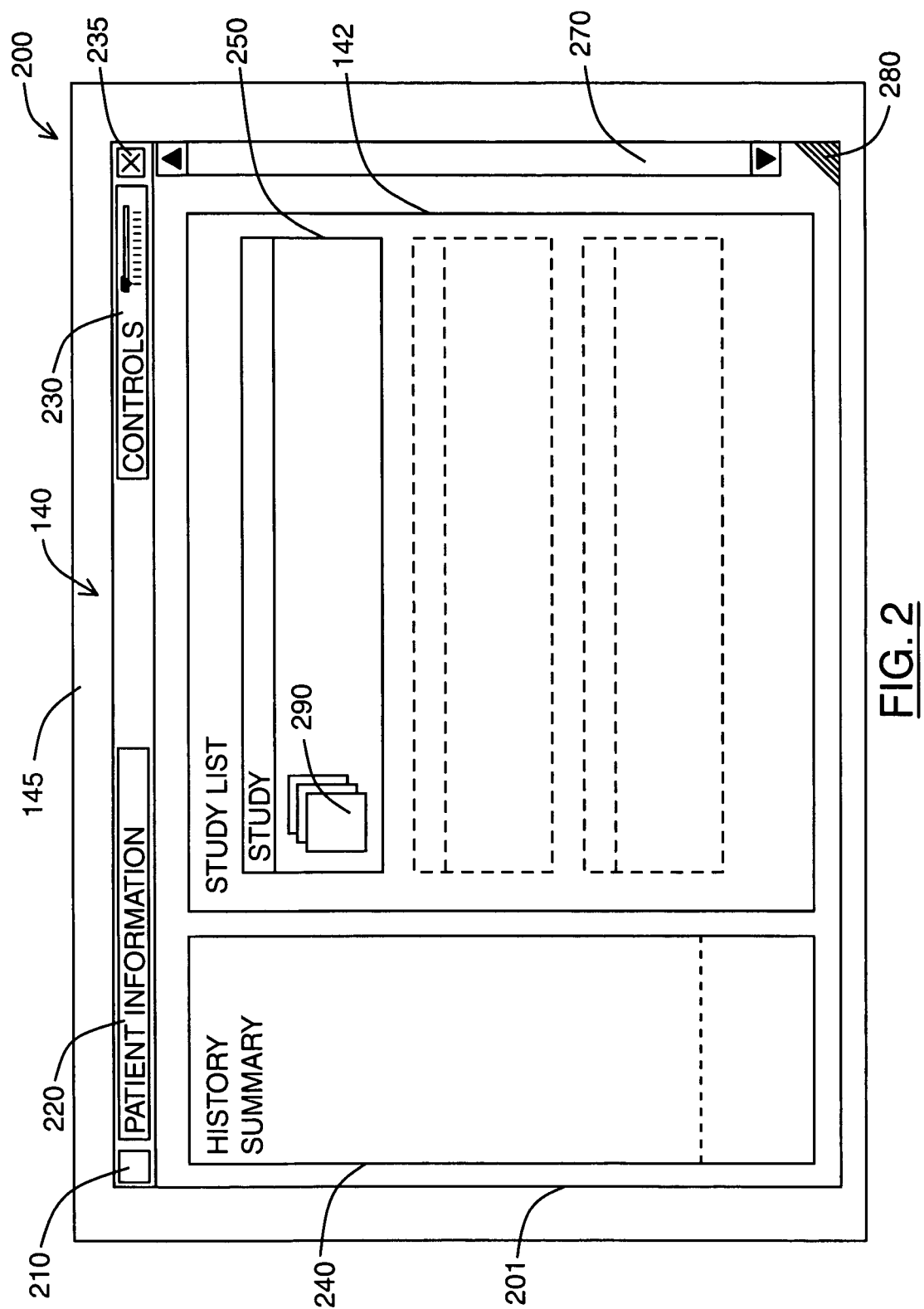
FIG. 2 is a schematic diagram illustrating the interface generated by one exemplary embodiment of the imaging history display system of FIG. 1.

FIG. 2 is a schematic diagram illustrating one exemplary embodiment 200 of the patient summary interface 140 and diagnostic interface 145 generated by display driver 132 of the imaging history display system 100. Patient summary interface 140 contains a control interface 201, an imaging history summary interface 240 and imaging study list 142. The patient summary interface 140 typically overlays diagnostic interface 145.

The control interface 201 contains user interface elements for delivering information to the user, allowing modification of the display and arrangement of patient summary interface 140 and controlling the display of data in the imaging study list 142.

These user interface elements include a manipulation area 210, for initiating the operation of moving the patient summary interface 140 to a new location on the display; a patient information display 220 for displaying information related to the current patient history under review (e.g. name, sex, birthday and identification number); a toolset area 230 which allows user 106 to perform various actions on displayed data; a close button 235 for closing the patient summary interface 140 to fully reveal images that may be displayed beneath it; a scroll bar 270 which may be displayed only when necessary to allow vertical scrolling through a plurality of imaging studies in imaging study list 142; and a resize control 280 for changing the vertical and horizontal dimensions of the patient summary interface 140. Imaging history summary interface 240 provides an iconic summary of imaging studies and arranges them in a compact reverse chronological manner, and is described in relation to FIG. 6 below.

Figure 3:
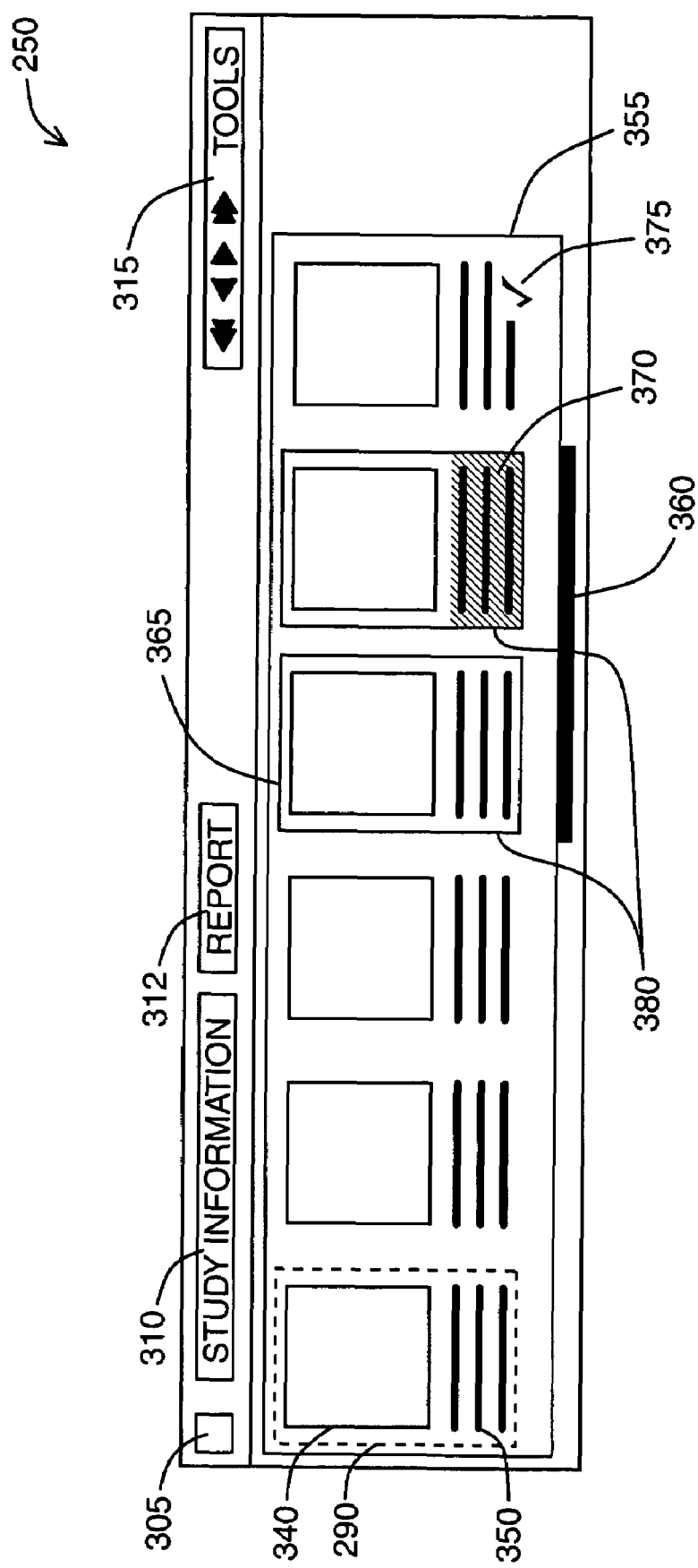
FIG. 3 is a schematic diagram of the image management tool displayed in the interface of FIG. 2 that is used to represent a single study.

Imaging study list 142 contains a list of one or more medical imaging studies 143. Referring now to FIG. 3, there is shown a more detailed schematic diagram of medical imaging study view 250. Each medical imaging study view 250 has an open control button 305, which when selected, opens the entire study into the diagnostic interface 145 (e.g. imaging series 290 in FIG. 2). If diagnostic interface 145 is configured for tabbed workspaces, clicking on open control 305 creates a new tab and displays the study 143 therein. If diagnostic interface 145 is configured for a windowed workspace, clicking on the open control 305 creates a new window and displays the study 143 therein.

As shown in FIG. 3, medical imaging study view 250 also displays study information 310 (e.g. a study number, date and time etc.); a reporting tool 312 for reviewing the reports of dictated studies as described above with respect to report module 130; and a contextual toolbar 315 for paging through the imaging series 290 and performing other operations, as described below. Each imaging series 290 is composed of a thumbnail image 340 and a text description 350, which may appear over multiple lines and contain information such as the series name, number of images in the series, time of series creation and slice thickness, where appropriate. A thumbnail image 340 consists of a representative image from a series of images. The thumbnail image 340 represents all of the images in a single series. The combination of the thumbnail image 340 and the thumbnail text description 350 will be referred to in the present disclosure as a "thumbnail".

Furthermore, medical imaging study view 250 may display visual cues to indicate the selection status or historical status of each imaging series 290, such as for example: the active view shading 370 which highlights the text description 350 for a particular series that is currently visible in the diagnostic interface 145; the selected study outline 355 which indicates that imaging series 141 from the imaging study 143 currently outlined by the thin line are selected in the patient summary interface 140 or diagnostic interface 145; the selected series outline 380 which indicates that images from the series currently outlined by the thin line are selected in diagnostic interface 145; and a viewed indicator 375 which indicates that a particular series has already been reviewed by a user 106 (e.g. a checkmark, etc.) in the diagnostic interface 145.

For PACS with color monitors 152, the selected study outline 355 is displayed in a color that matches the medical imaging study view 250 on patient summary interface 140 and diagnostic interface 145. Furthermore, contextual toolbar 315 displays varying options depending on the selection status of the instant imaging study. If an imaging study is not selected, contextual toolbar 315 is not visible. If an imaging study is selected, but not visible in diagnostic interface 145, only a subset of the features of toolbar 315 will be available. Additionally, text within a study, such as text description 350 or study information 310, appears as a brighter color or brighter shade of gray if that study is currently in view in the diagnostic interface 145.

Figure 4A:
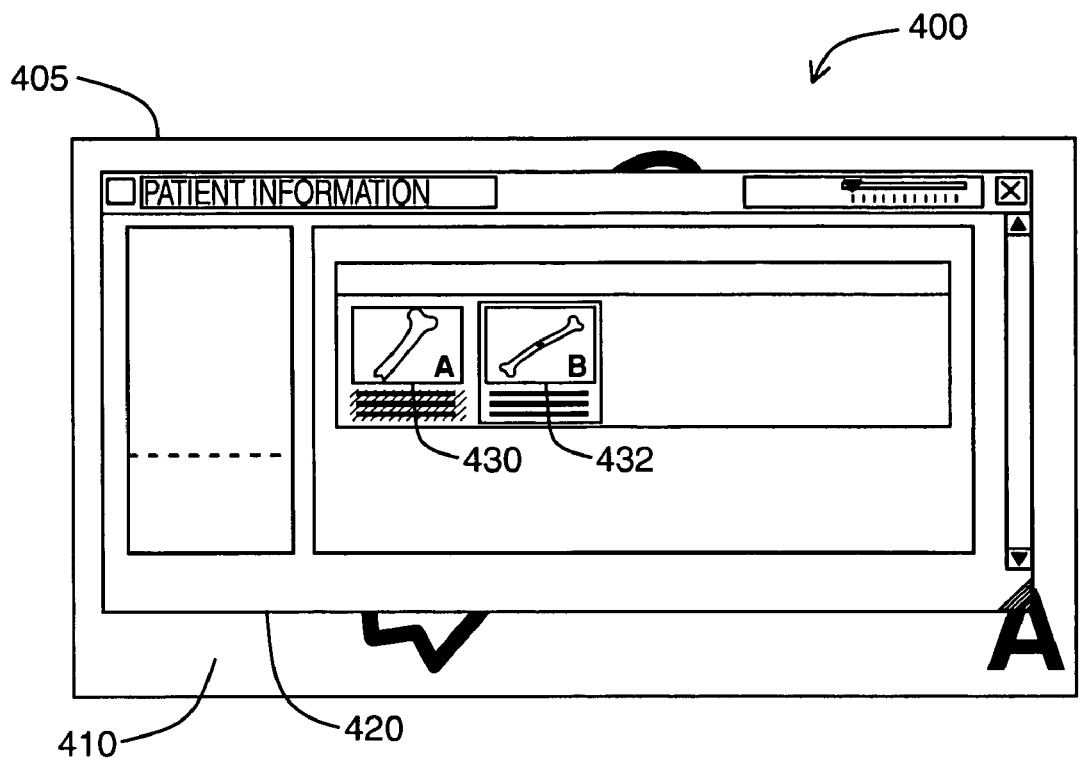
FIGS. 4A, 4B, 4C and 4D are schematic diagrams illustrating a method for changing the actively displayed image in the interface of FIG. 2.
Figure 4B:
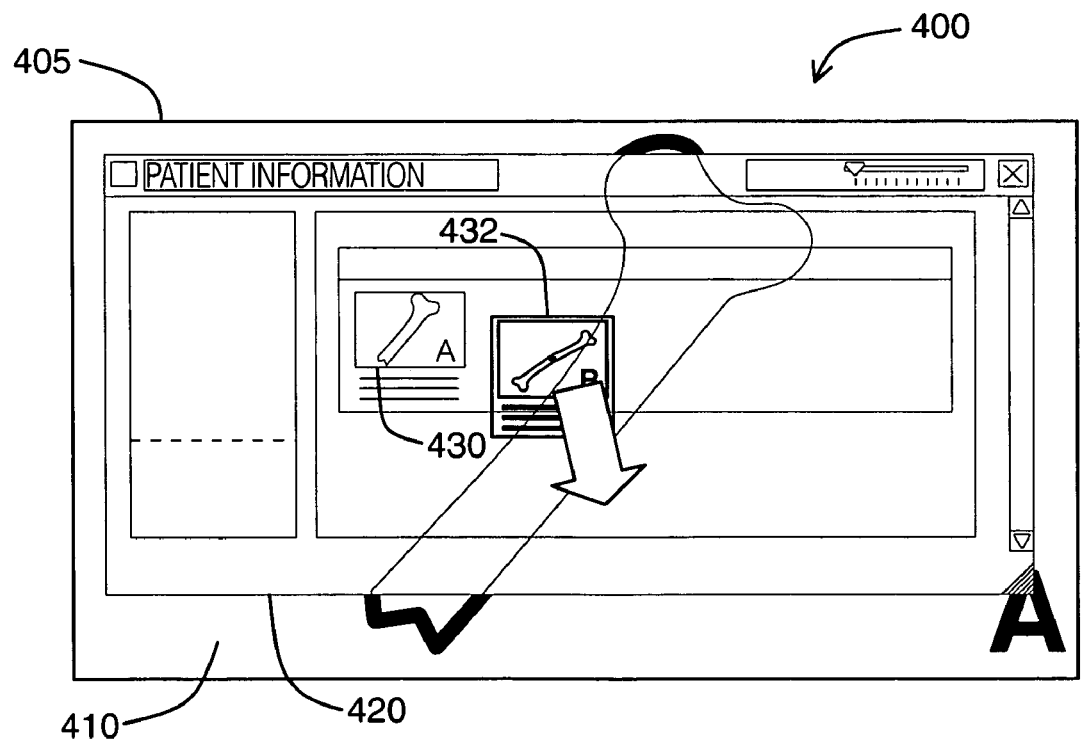
Figure 4C:
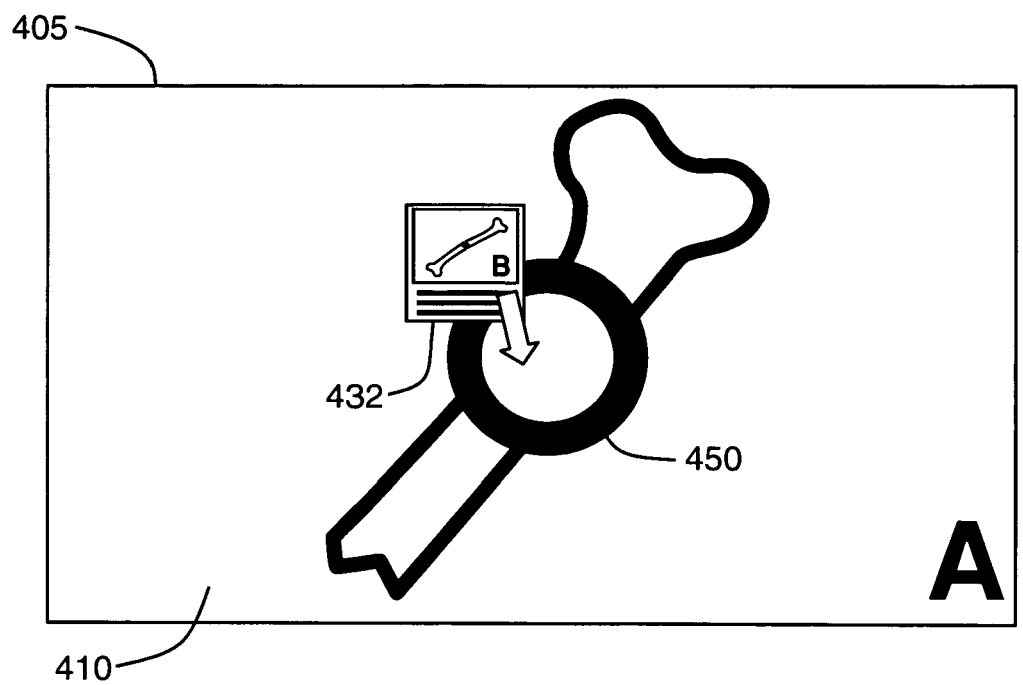
Figure 4D:
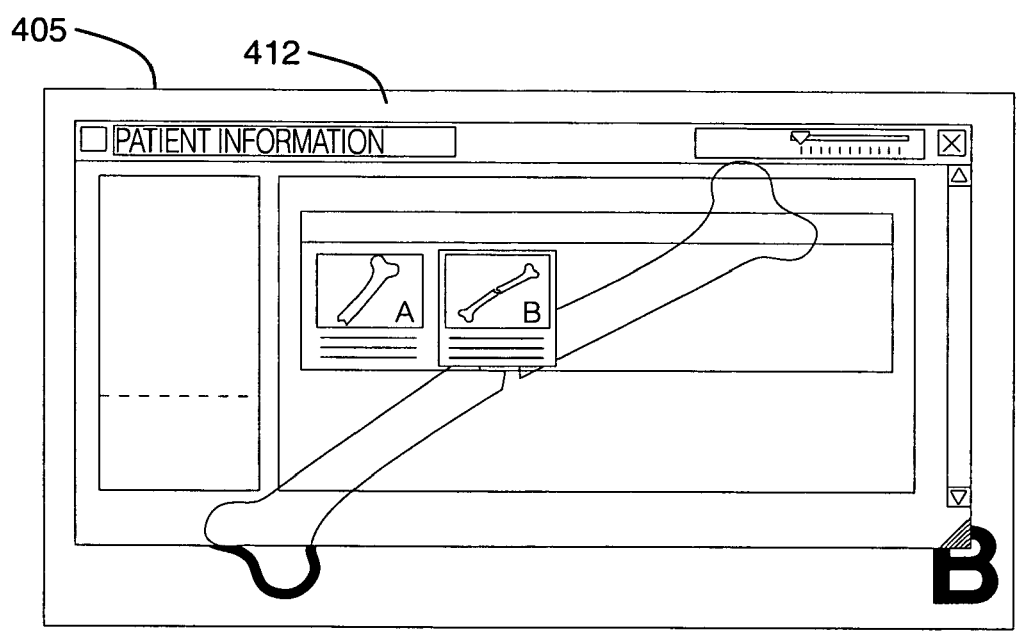
Figure 5:
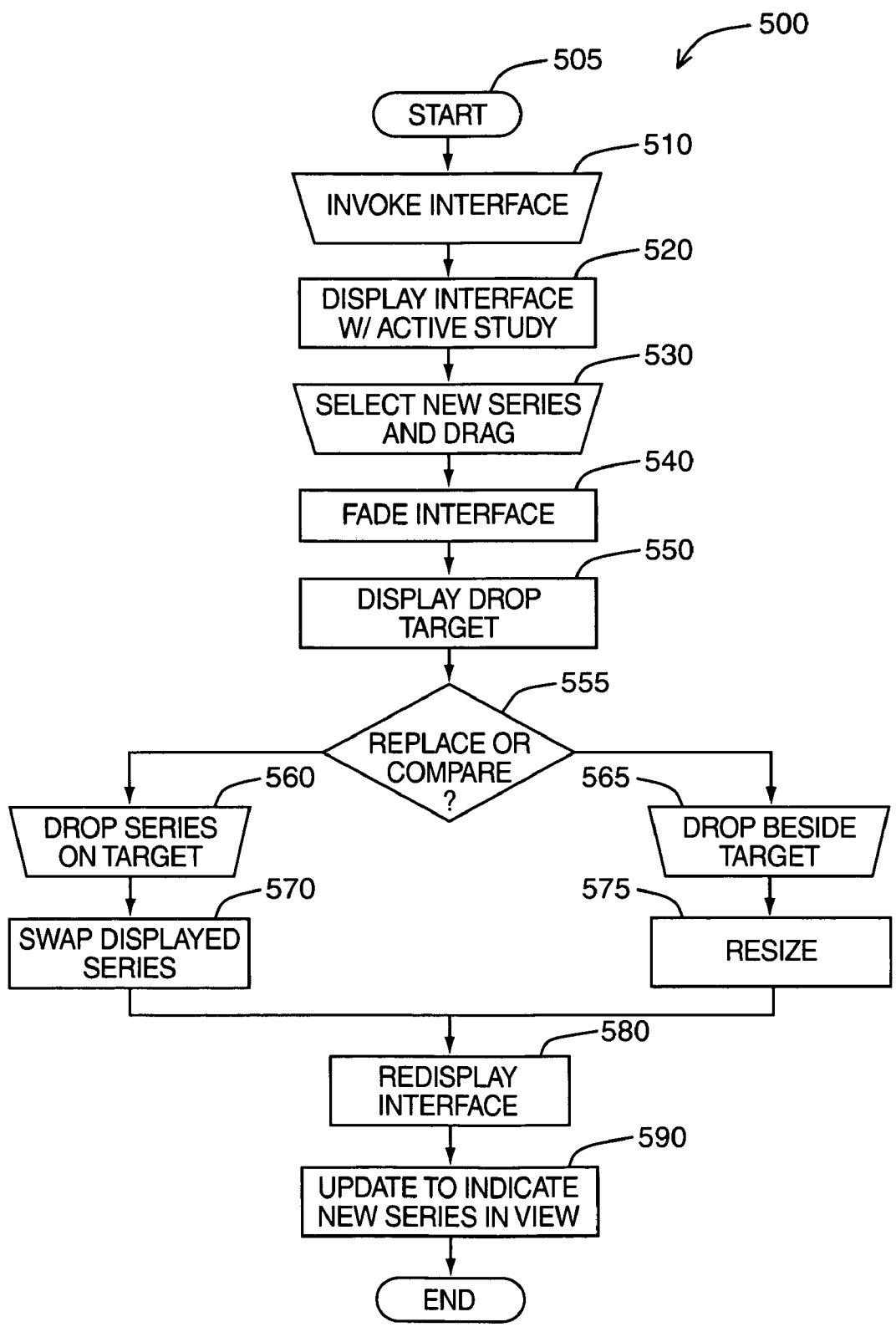
FIG. 5 is a flowchart diagram illustrating the operational steps executed by the imaging history display system performing the method of FIGS. 4A, 4B, 4C and 4D, according to the swap module of FIG. 1.

Referring now to FIGS. 4A, 4B, 4C, 4D, and 5, there is illustrated a method for changing the actively displayed image in the diagnostic interface 145 using the swap module 122. Specifically, FIG. 5 is a flowchart diagram illustrating the process steps 500 that are executed by swap module 112 and image processing module 110 to provide image swap functionality between patient summary interface 140 and diagnostic interface 145 when user 106 selects an imaging series 141 for display.

The process begins at step (505). At step (510), user 106 invokes an interface, such as patient summary interface 145. The interface is displayed at step (520) and indicates any selected (or active) studies.

FIG. 4A illustrates a diagnostic interface 405, corresponding to diagnostic interface 145, overlaid with patient summary interface 420, corresponding to patient summary interface 140, such that patient summary interface 420 obscures a currently displayed medical image 410 from a medical imaging series represented by thumbnail 430. Also shown is a thumbnail 432 corresponding to another medical imaging series. In this illustration, it is assumed that the user 106 wishes to change the actively displayed imaging series in diagnostic interface 405 from the series represented by thumbnail 430 to that represented by thumbnail 432.

To change the actively displayed series, user 106 selects and begins to drag thumbnail 432 away from its point of origin at step (530) as graphically shown in FIG. 4B. As thumbnail 432 is moved, the opacity of patient summary interface 420 is reduced at step (540), such that the currently displayed medical image 410 is less obscured and more visible. As thumbnail 432 is dragged progressively further from its point of origin, patient summary interface 420 grows progressively less opaque, until it finally disappears (FIG. 4C). Simultaneously, at step (550), a drop target 450 appears to indicate where a swap can be activated. With patient summary interface 420 now completely invisible, user 106 can drag thumbnail 432 toward the drop target 450. The color of drop target 450 corresponds to the color used for selected study outline 355 and selected series outline 370.

At step (555), user 106 may choose either to change the imaging series 141 in view on diagnostic interface 405 or to position a new imaging series 141 adjacent to the currently displayed imaging series 141, to facilitate comparison. If the decision is to replace the current imaging series 141 (i.e. engage in a "swap") then user 106 drags thumbnail 432 in close proximity to the drop target 450 and releases the mouse button at step (560) to complete the drag-and-drop operation.

With the mouse button released, medical imaging series 410 is substituted with a medical imaging series 412, at step (570).

Alternatively, user 106 drags thumbnail 432 onto diagnostic interface 145, but not onto drop target 450, and releases the mouse button at step (565). Swap module 122 resizes imaging series 141 on diagnostic interface 405 to fit all images within the available display area at step (575). This allows the user 106 to quickly compare two imaging series 141 side by side.

Subsequently, the opacity of patient summary interface 140 begins to increase at step (580) as shown in FIG. 4D, such that it fades back into view, obscuring medical image 412. Patient summary interface 140 is updated to indicate the new actively displayed image(s) at step (590), and may be dismissed by selection of the toolbar close button 235, mouse button, or shortcut key, or the like, to allow for unencumbered diagnostic viewing.

Figure 6:
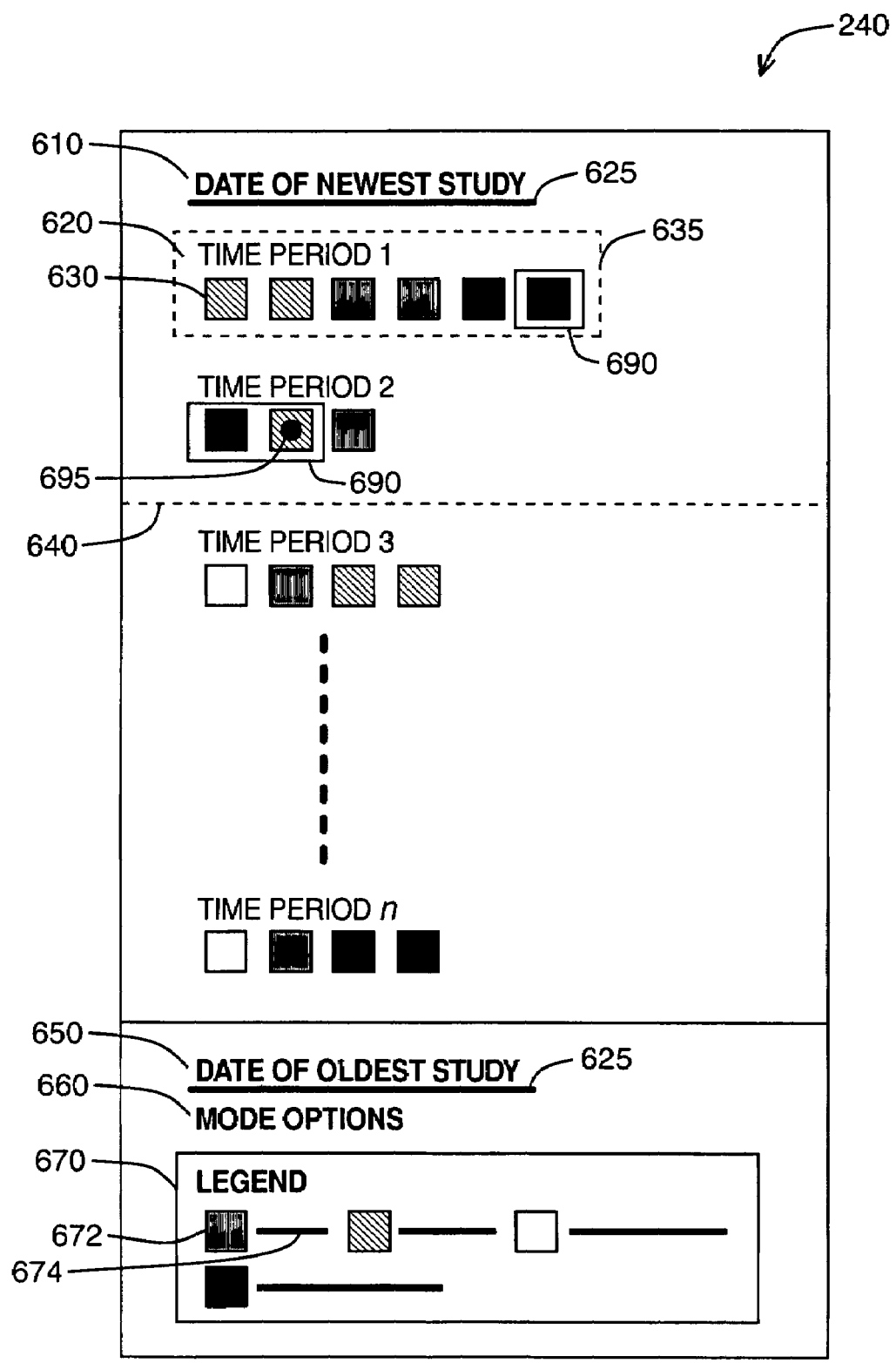
FIG. 6 is a schematic diagram of the study dataset history tool provided by the imaging history display system of FIG. 2.
Figure 7:
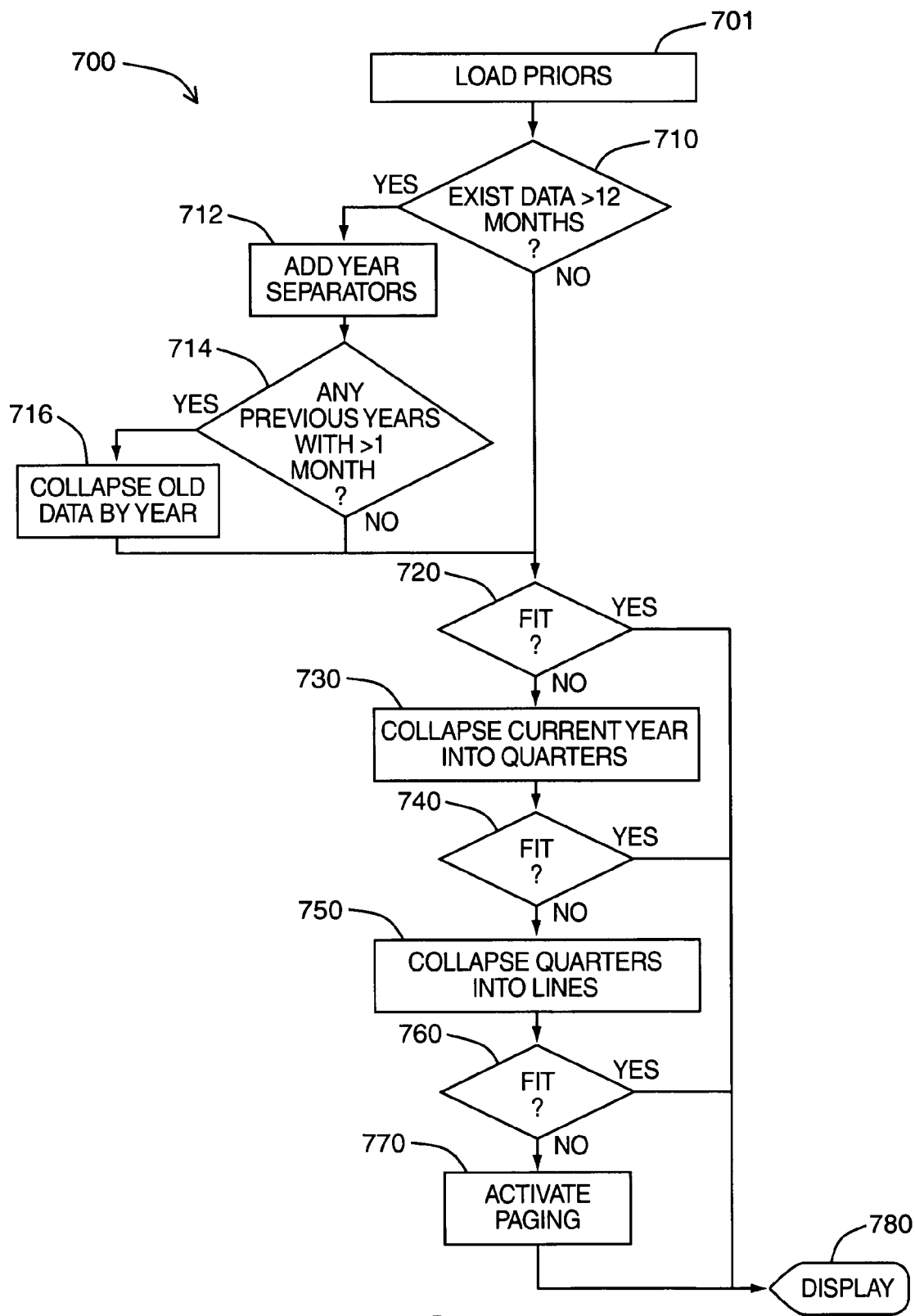
FIG. 7 is a flowchart diagram illustrating the operational steps executed by the study dataset history tool of FIG. 6 in generating a display, according to the history module of FIG. 1.

Referring now to FIGS. 6 and 7, there is illustrated an imaging history summary interface 240 generated in part by history module 128. FIG. 6 is a schematic diagram that illustrates how imaging history summary interface 240 provides a snapshot view of all imaging studies of interest in the PACS for a given patient. The patient imaging studies are arranged vertically in such a manner as to display as much relevant information as possible in the current interface area without the need for a scroll bar.

At the top of the imaging history summary interface 240 the DATE OF NEWEST STUDY indicator 610 is displayed to indicate the month and year of the newest imaging study. Following the DATE OF NEWEST STUDY indicator 610, there are arranged, in reverse chronological order, one or more study icons 630 representing extant imaging studies. Underneath these study icons 630, a DATE OF OLDEST STUDY indicator 650 is displayed, followed by a contextual MODE OPTIONS list 660 and a LEGEND 670.

Each study icon 630 corresponds to exactly one imaging study view 250 and is colored to indicate a particular modality or body part, depending on the current display mode of the imaging history summary interface 240. Each study icon 630 is grouped according to its temporal relationship with other study icons 630 to create one or more time period groups 635. These time period groups 635 are identified by one or more time period indicators 620. Time period indicators 620 provide the month and year of a group (e.g. "August 2005") or, alternatively, only the year. In the case where time period groups 635 span more than one year, one year or more separator 640 is displayed within imaging history summary interface 240 to separate time period groups 635, by year, as appropriate.

If there is overflow, one or both of the newest study indicator 610 and oldest study indicator 650 becomes a paging hyperlink 625 (FIG. 6) which allow the user 106 to adjust date ranges of imaging studies within the viewable area of imaging history summary interface 240. Before paging hyperlinks 625 are enabled, certain formatting rules are employed to condense information to fit within the viewable area of imaging history summary interface 240, beginning with the least relevant data.

The formatting of time periods is conducted according to certain time period formatting rules. For example, if there is enough room in the imaging history summary interface 240, then the view of all study icons 630 is expanded to show all of the imaging studies by month, up to 12 months back from a current date. If a previous year has imaging studies that span over more than one month then the year is only identified, but as discussed above, a line separator is provided between the years.

If a patient has many imaging studies, then the history module 128 will start to compress the time periods to show as much within the imaging history summary interface 240 as possible. For example, for the 12 months back from the current date, the time periods will be compressed from months into quarters (i.e. under time period headings "within 3 months", "within 6 months", "within 9 months", "within 1 year", etc.). Since the individual month headings have been removed from display, study icons 630 are shown month by month on separate lines underneath the quarterly time period headings. Then, going back, the rest of the time periods will be provided year by year (e.g. time period headings "2003", "2002", etc.) Again, if imaging studies from more than one year are shown, a line is displayed in between the years.

Further, it is possible to further compress collapsed quarters by arranging study icons 630 grouped together underneath quarterly time period headings (e.g. "within 3 months", "within 6 months", etc.) so that they flow together sequentially along a line without separate line breaks for differing months. This is contrast to the regular display under quarterly time period headings discussed above where study icons 630 associated with different months are displayed on separate lines. According to this formatting style, while the study icons 630 flow together, those associated with different months are optionally separated by space breaks in the line. This way it is possible to show more years on-screen.

Accordingly, various time period formatting rules or "heuristics" are employed by imaging history summary interface 240. The following time period formatting rules are provided to be illustrative only and it should be understood that many other rules could be utilized in place of or in combination with the following rules.

First, the basic principle of showing as much of the patient history onscreen as possible is observed even if this requires compression of time periods, as discussed above. Also, imaging studies are always displayed backwards in time from the most recent exam to the least. Few details of the imaging study are shown, except the box that indicates by its color, the modality of the imaging study and by its location its gross time period. Time periods are skipped if no imaging studies are available for those time periods. Months are collapsed to quarters to years and the quarters are labeled not by date but by the time period headings "within 3 months", "within 6 months", etc. When space within the imaging history summary interface 240 is scarce, the quarterly view is collapsed to a "compressed" quarterly view (where as discussed above, the imaging studies are shown to flow together sequentially along a line instead of being positioned on new lines). If the only imaging studies within a particular year fall within one particular month, then the particular month and year is shown on the time period heading. Finally, only the current year is shown in the month or quarterly formats.

Study icons 630 corresponding to imaging studies currently available on the diagnostic interface 145 are optionally highlighted by a highlight outline 690 (e.g. lined box shown in FIG. 6), with the study currently in view further indicated by an active study indicator 695 (e.g. a dot as shown in FIG. 6).

Contextual MODE OPTIONS list 660 provides a number of hyperlinks to change or arrange the display of imaging studies within imaging history summary interface 240 according to particular criteria. These criteria can include, for example, showing all available studies ("Show all"), limiting the display of imaging studies to relevant prior studies only ("Show only relevant"), displaying imaging studies by modality ("Show by modality") or displaying imaging studies by body part ("Show by body part"), etc.

For example, imaging history summary interface 240 is designed to operate by default to display only relevant imaging studies. Relevancy of imaging studies is determined in accordance with relevancy module 125, as described in detail below with respect to FIGS. 17A and 17B below. In this default mode, the hyperlink "Show all" is displayed within the contextual MODE OPTION list 660. If the user 106 selects the "Show all" hyperlink then the imaging history summary interface 240 will display all prior imaging studies for that patient. The hyperlink "Show relevant" will then be displayed within the contextual MODE OPTION list 660.

As discussed above, the contextual MODE OPTIONS list 660 can also include hyperlinks that allow the user 106 to display imaging studies by modality ("Show by modality") or by body part ("Show by body part"). Depending on whether the "Show by modality" or the "Show by body party" MODE OPTION is selected (or provide by default), a LEGEND 670 will display an appropriate list of legend icons 672 and a description 674 for each, to disclose the meaning of each icon 630. The legend icons 672 within the LEGEND 670 are color coded (or grayscale coded) to assist the user 106 in identifying which study icons 630 displayed above the LEGEND 670 have the characteristics (e.g. body part or modality identity, etc.) identified by the particular legend icons description 674 (e.g. "Hip", "Pelvis", or "CT", etc.). Optionally, the LEGEND 670 is designed to only allow a limited number (e.g. 3) of legend icons 672 to be displayed at one time. In such a case the user 106 could "hover" over the LEGEND 670 to obtain a full legend in a "popup" box (not shown).

Optionally, the imaging history summary interface 240 is designed to operate by default to show prior imaging studies within imaging history summary interface 240 by body part and the MODE OPTION "Show by modality" is displayed. Again, the legend icons 672 will each represent a body part (e.g. "Hip", "Pelvis", "Abdomen", "Knee", etc.) and through color coding (or grayscale coding) be clearly identifiable with certain study icons 630 displayed above the imaging history summary interface 240.

If the user 106 selects the "Show by modality" hyperlink then the imaging studies are shown within imaging history summary interface 240 by modality and the link changes to "Show by body part". Again, the legend icons 672 will each represent a modality (e.g. "CT", "MRI", etc.) and through color coding (or grayscale coding) be clearly identifiable with certain study icons 630 displayed above the imaging history summary interface 240.

Finally, the user 106 can use the imaging history summary interface 240 to navigate to prior imaging studies that he wants to use for comparison. Specifically, the user 106 would move his cursor to the position of a study icon 630 and then by hovering over the study icon 630, the user 106 can cause a "popup" box to be displayed that contains more details about the specific imaging study represented by the study icon 630. Based on these details, the user 106 can then decide to select the study icon 630 to display the imaging study on the right side of the imaging history summary interface 240 and make that imaging study the "active" study.

FIG. 7 is a flowchart diagram illustrating the operational steps 700 executed by history module 128 to fit as much information as possible within the viewable area of imaging history summary interface 240. The process begins at step (701), by loading prior imaging studies.

At step (710), a test is performed to determine if there are any prior imaging studies more than 12 months old. If there are no studies older than 12 months, the process proceeds to step (720). Otherwise, a separate branch is followed, beginning at step (712). At step (712), year separators are added to the display, to facilitate identification of older data. Next, a test is performed to determine if there are previous years containing only imaging studies from a single month, at step (714). If no, the process proceeds to step (720). Otherwise, data from each of the years with more than one month of imaging studies is collapsed into a single group for each year at step (716) and the process proceeds to step (720).

At step (720), a test is performed to determine if all imaging studies will fit in the viewable area of imaging history summary interface 240. If yes, information is displayed at step (780). If not, imaging studies from the current year have their date identifiers stripped and are collapsed into quarters, with each quarter identified by its relative date range (e.g., "less than 3 months ago"), at step (730).

At step (740), a test is performed to determine if all imaging studies will fit in the viewable area of imaging history summary interface 240. If yes, information is displayed at step (780). If not, imaging studies for each quarter are further condensed by removing line breaks between quarters, at step (750).

At step (760), a test is performed to determine if all imaging studies will fit in the viewable area of imaging history summary interface 240. If yes, information is displayed at step (780). If not, paging hyperlinks, such as those described above are activated at step (770), and information is displayed at step (780).

Figure 8A:
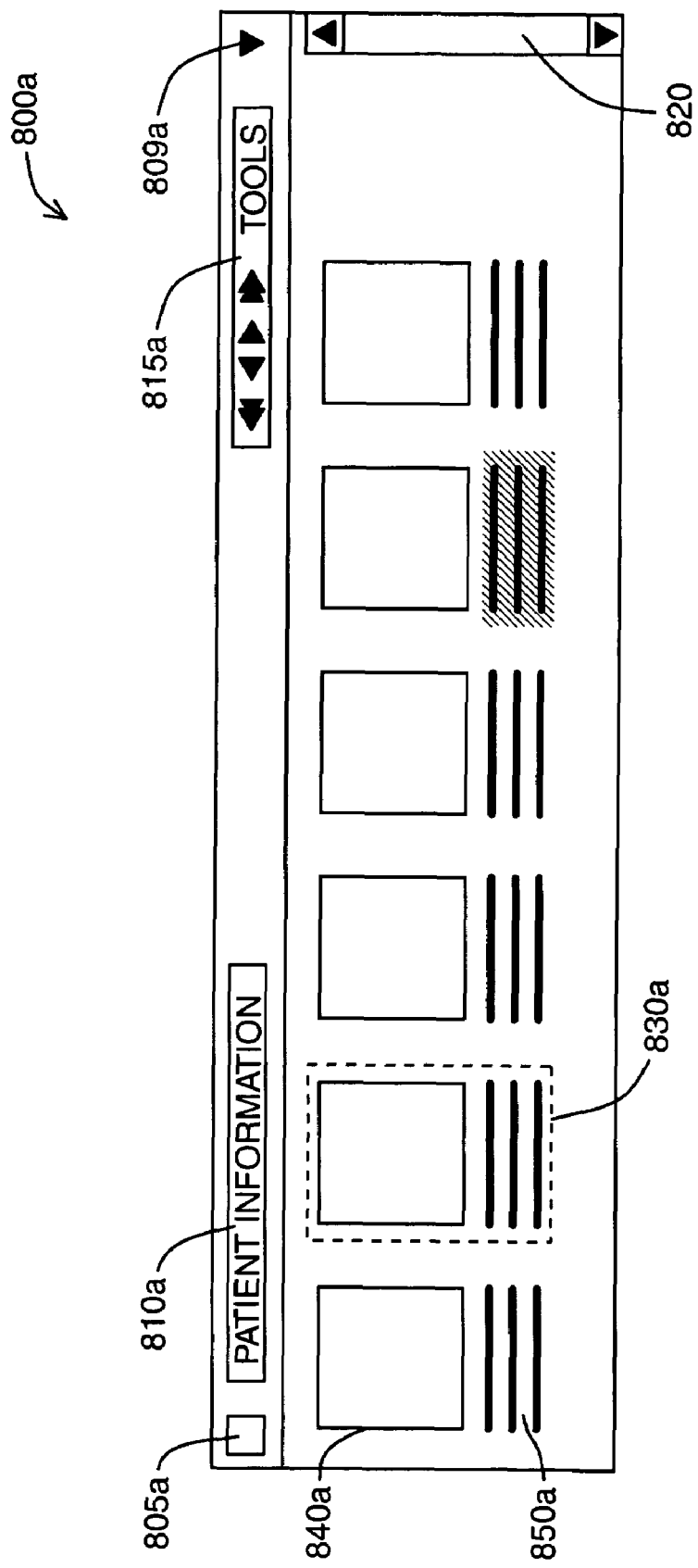
FIGS. 8A and 8B are schematic diagrams of two embodiments of the condensed display of the image management tool of FIG. 3.
Figure 8B:
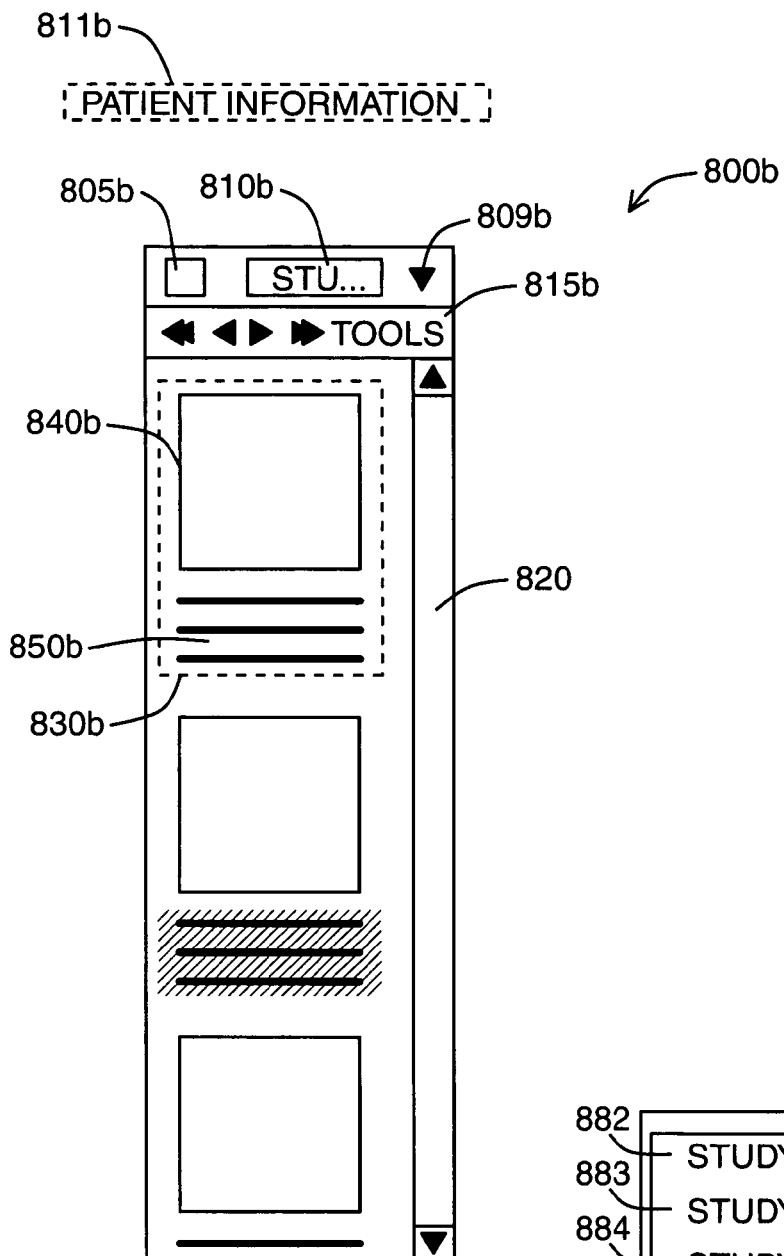

Referring now to FIGS. 8A and 8B, the patient summary interface 140 may be condensed or docked by user 106 to a vertical or horizontal edge (e.g. top, bottom, left or right side) of diagnostic interface 145, to retain some display elements while eliminating others and therefore facilitate effective display of underlying medical diagnostic images 147.

FIG. 8A illustrates the patient summary interface 140 in a horizontal docked patient summary interface mode 800a, which is generated by dock module 124 when user 106 drags patient summary interface 140 to the top or bottom edge of diagnostic interface 145, using manipulation area 210 and imaging history display system 100 enters into a "docked mode". In horizontal docked patient summary interface mode 800a, ordinary features of patient summary interface 140, such as imaging history summary interface 240 and non-selected medical imaging study views 250 are omitted to minimize required display area and to focus only on the imaging study 143 on the active screen.

Otherwise, horizontal docked patient summary interface mode 800a contains primarily the same functional elements as a normal patient summary interface 140, including: manipulation area 805a, corresponding to manipulation area 210; patient data display 810a, corresponding to patient data display 220; toolset area 815, corresponding to toolset area 230; and display entities 830a, corresponding to display entities 147 and containing a thumbnail image 840a and text description 850a.

FIG. 8B illustrates patient summary interface 140 in a vertical docked patient summary interface mode 800b, which is generated by dock module 124 when user 106 drags patient summary interface 145 to the left or right edge of diagnostic interface 145, using manipulation area 210. In vertical docked patient summary interface mode 800b, ordinary features of patient summary interface 145, such as imaging history summary interface 240 and non-selected medical imaging study views 250 are omitted to minimize required display area and focus only on the selected studies.

Otherwise, vertical docked patient summary interface mode 800b contains primarily the same functional elements as a normal patient summary interface 140, including: manipulation area 805b, corresponding to manipulation area 210; patient data display 810b, corresponding to patient data display 220; toolset area 815, corresponding to toolset area 230; and display entities 830b, corresponding to display entities 147 and containing a thumbnail image 840b and text description 850b.

Vertical docked patient summary interface mode 800b is necessarily constrained to a narrow width, but only vertical scroll bars 820 are displayed. Dock module 124 arranges elements such as patient data display 810b and toolset area 815 in a vertically stacked arrangement. In particular, patient data display 810b may not fit in the available horizontal display area, therefore text will be truncated in the display. The full text of patient data display 810b is revealed when user 106 performs a mouse "hover" operation, that is placing the input device 154 (e.g. mouse) cursor over the truncated text for a predetermined length of time (e.g. 2 seconds). In response to a hover action, dock module 124 temporarily displays an ancillary text display 811b, containing the full text of patient data display 810b until user 106 terminates the hover action.

Figure 9A:
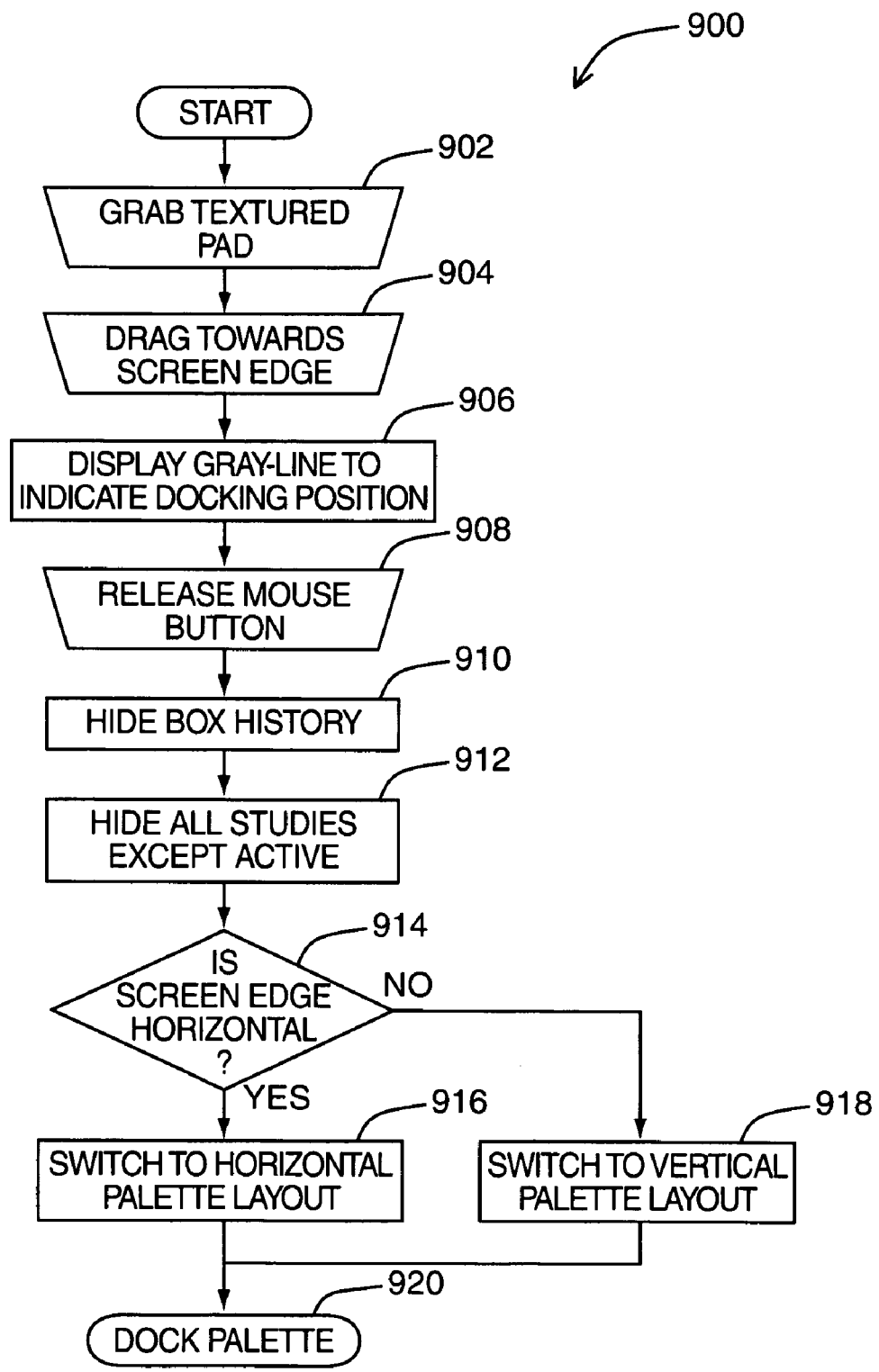
FIGS. 9A and 9B are flowchart diagrams illustrating the operational steps executed by the imaging history display system of FIG. 2 in choosing a display mode for the image dataset series management tools of FIGS. 3, 8A and 8B, according to the docking module of FIG. 1.

To initiate docked patient summary interface mode, the operational steps 900 shown in the flowchart diagram illustrated in FIG. 9A are followed. User 106 uses input device 154 to select manipulation area 805a or 805b at step (902) and performs a drag operation towards a horizontal or vertical edge (i.e. top, bottom, left or right side) of diagnostic interface 145 at step (904). When the manipulation area 805a or 805b has been dragged close to one edge, dock module 124 displays a gray-line to indicate a potential docking position, at step (906). If user 106 desires this location for a docking position, the mouse button is released at step (908). Dock module 124 then hides imaging history summary interface 240 at step (910) and hides all studies 141 except those actively displayed on diagnostic interface 145, at step (912).

Dock module 124 evaluates if the indicated screen edge is a vertical screen edge (i.e., left or right) or a horizontal screen edge (i.e., top or bottom), at step (914). If the indicated screen edge is horizontal, horizontal docked patient summary interface mode 800a is enabled at step (916). Otherwise, vertical docked patient summary interface mode 800b is enabled at step (918). The docked patient summary interface mode becomes ready for use at step (920).

While in docked patient summary interface modes 800a or 800b, a second patient summary interface mode 140 may be invoked by user 106 in addition to the docked patient summary interface mode interfaces. Additional patient summary interfaces 140 may also be docked using dock module 124 and the procedures outlined above.

Figure 9B:
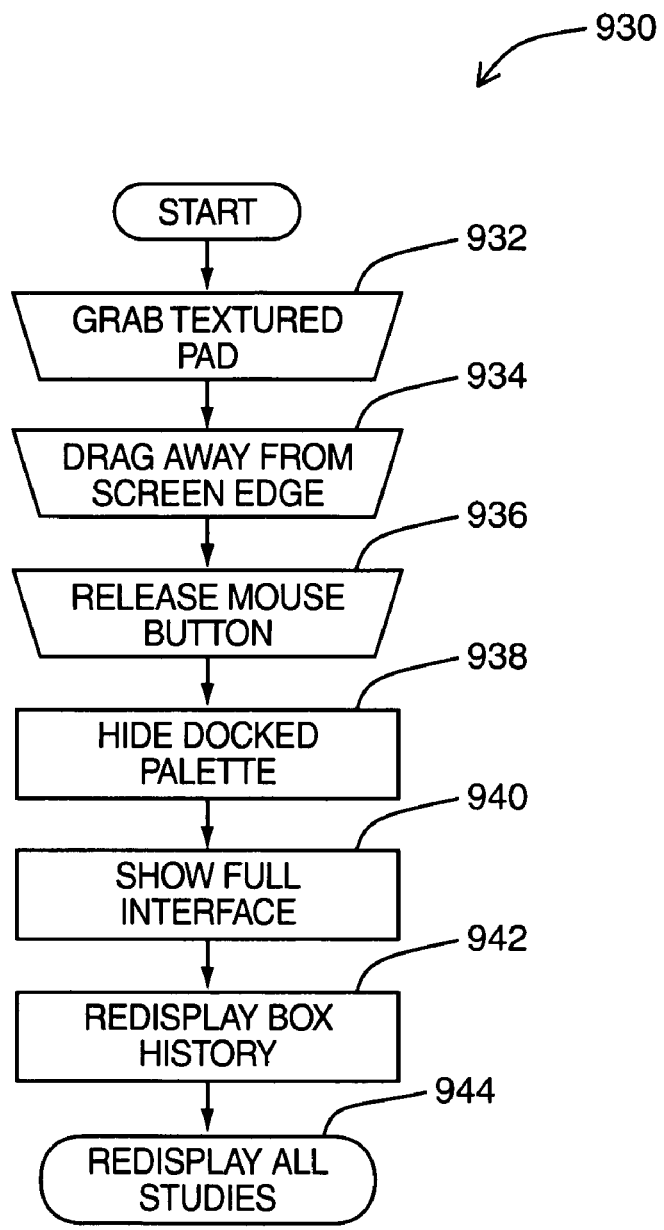

FIG. 9B illustrates the operational steps 930 associated with termination of docked patient summary interface modes 800a or 800b. User 106 uses input device 154 to select manipulation areas 805a or 805b at step (932) and performs a drag operation away from the edges of diagnostic interface 145 at step (934), releasing the device button when the manipulation area 805a or 805b has been dragged towards the centre of the display area, at step (936). When the user drafts the interface away from the edge, the entire interface is shown once again. Dock module 124 then hides the docked patient summary interface mode 800a or 800b, at step (938), and redisplays patient summary interface 140 at step (940). Imaging history summary interface 240 and imaging study list 142 are redisplayed at steps (942) and (944), respectively.

Figure 8C:
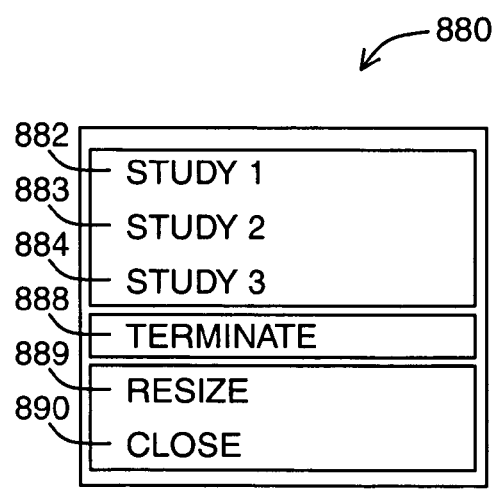
FIG. 8C is a schematic diagram illustrating the contextual menu of the image management tool of FIG. 3.
Figure 9C:
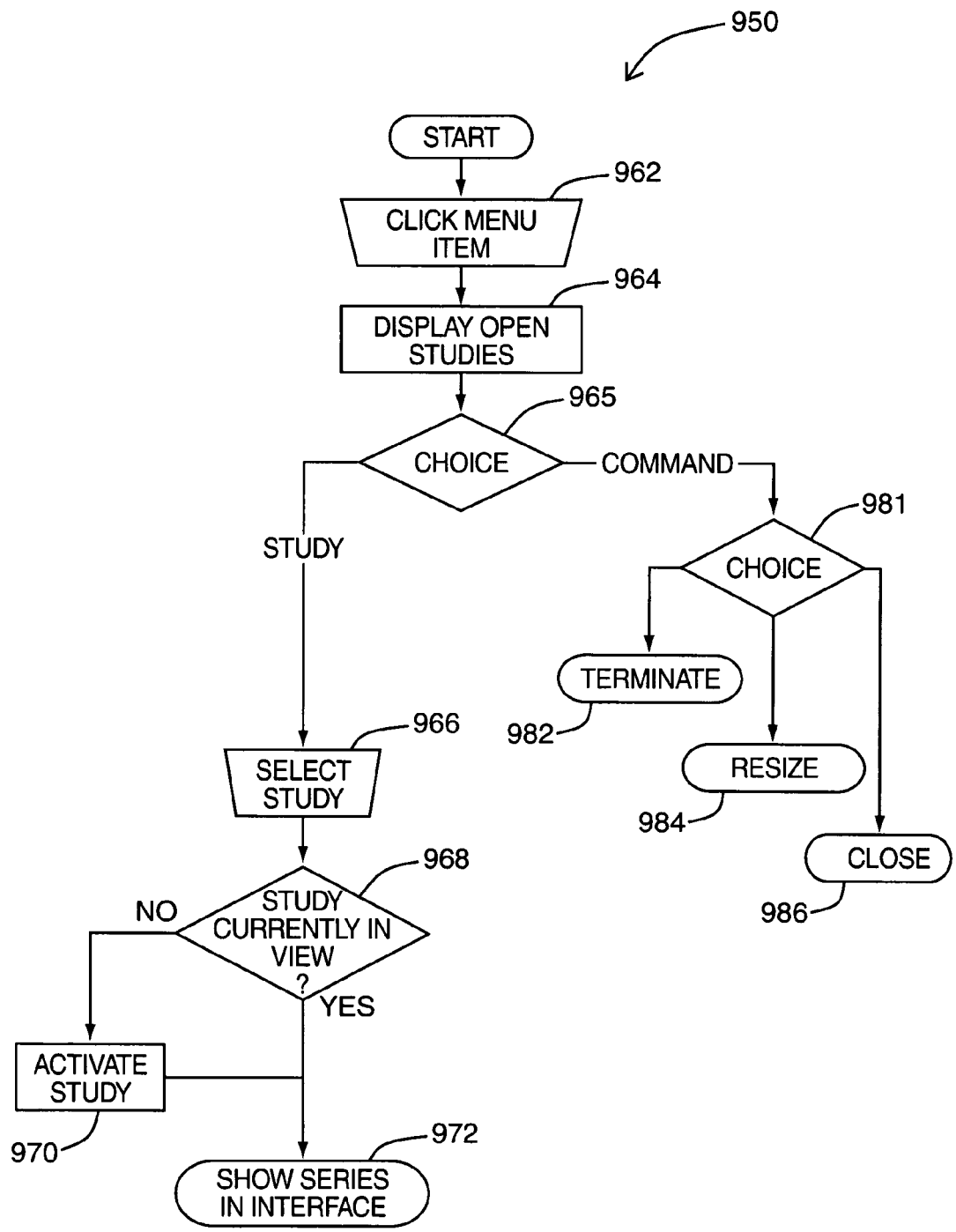
FIG. 9C is a flowchart diagram illustrating the operational steps executed by the image display and management tool of FIGS. 3, 8A and 8B.

FIG. 9C is a flowchart diagram illustrating the process for using and operational steps 950 of a contextual menu 880 (FIG. 8C) that is available while docked patient summary interface mode 800a or 800b is active. The contextual menu 880 (FIG. 8C) can be displayed by user 106 through clicking on contextual menu arrow 809A or 809B. User 106 clicks contextual menu arrow 809A or 809B to invoke contextual menu 880 at step (962). Dock module 124 displays a list of open imaging studies and command options at step (864). Command options include "terminate docking mode" 888, "resize docking mode display" 889 and "close patient summary interface" 890, as illustrated in FIG. 8C.

At step (966), user 106 decides to either select a study for display from the open imaging studies list or invoke one of the available commands 888, 889 or 890. If user 106 chooses to select a study 882, 883 or 884 for display, the selection is made at step (966) and dock module 124 determines if the study is already in view in diagnostic interface 145 at step (968). If the study is currently not in view, it is brought into view at step (970). In either case, the study 882, 883 or 884, which was selected for display in diagnostic interface 145, is commensurately displayed in docked patient summary interface mode 800a or 800b in the appropriate form, at step (972).

If user 106 chooses a command option 888, 889 or 890 at step (965), dock module 124 determines which command was delivered at step (981). If "terminate docking mode" 888 was chosen, the docked patient summary interface mode termination procedure, outlined above, is carried out at step (982), resulting in the redisplay of the full patient summary interface 140. If "resize docking mode display" 889 was chosen, a resize function is initiated by dock module 124 at step (984), allowing user 106 to reshape the dimensions of docked patient summary interface 800a or 800b. If "close patient summary interface" 890 was chosen, the docked patient summary interface 800a or 800b is closed at step (986) and no patient summary interface 140 is displayed, either.

Figure 10A:
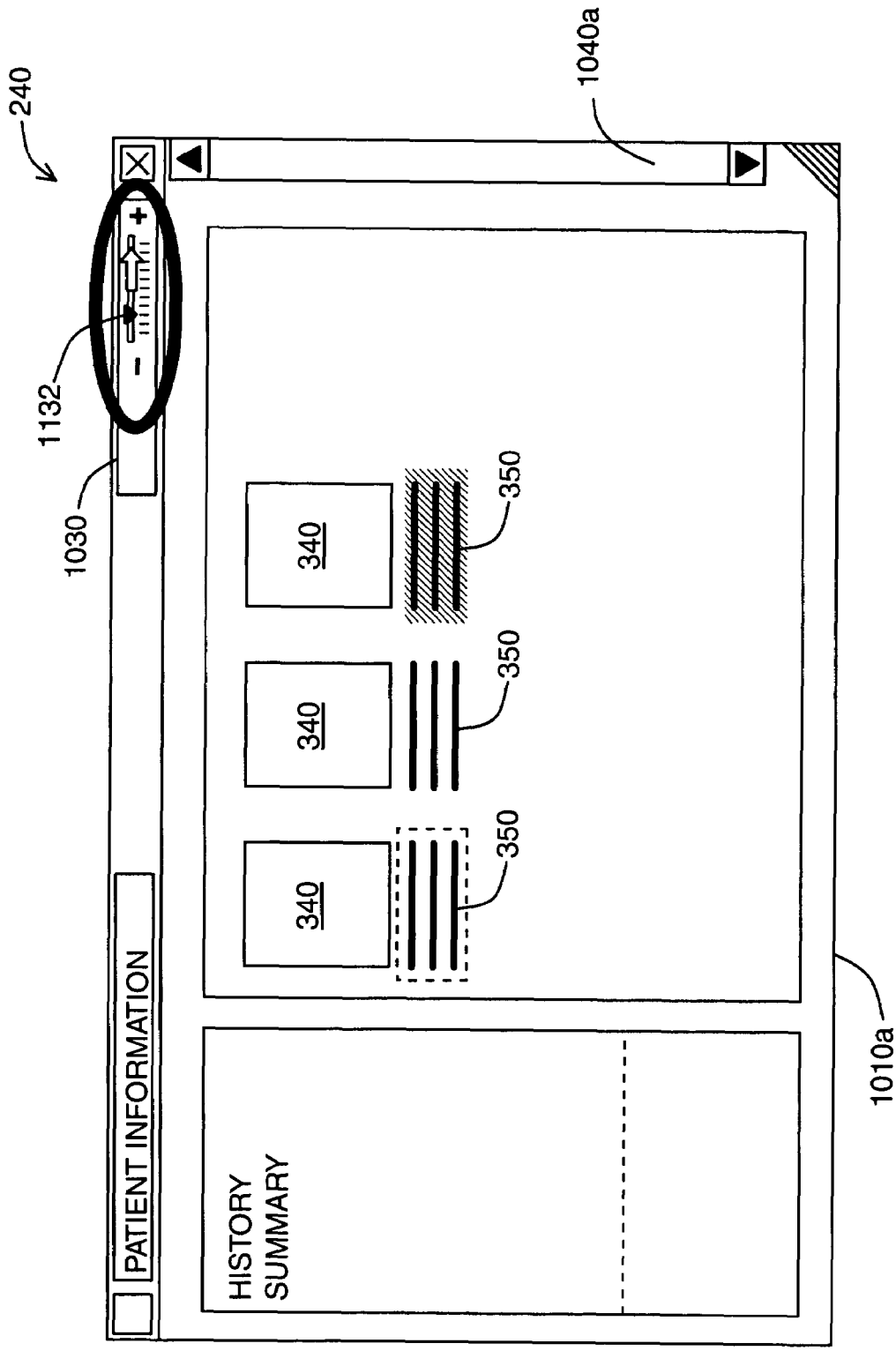
FIGS. 10A and 10B are schematic diagrams illustrating a method for changing the arrangement of displayed image dataset series in the image dataset series management tool of FIG. 3.
Figure 10B:
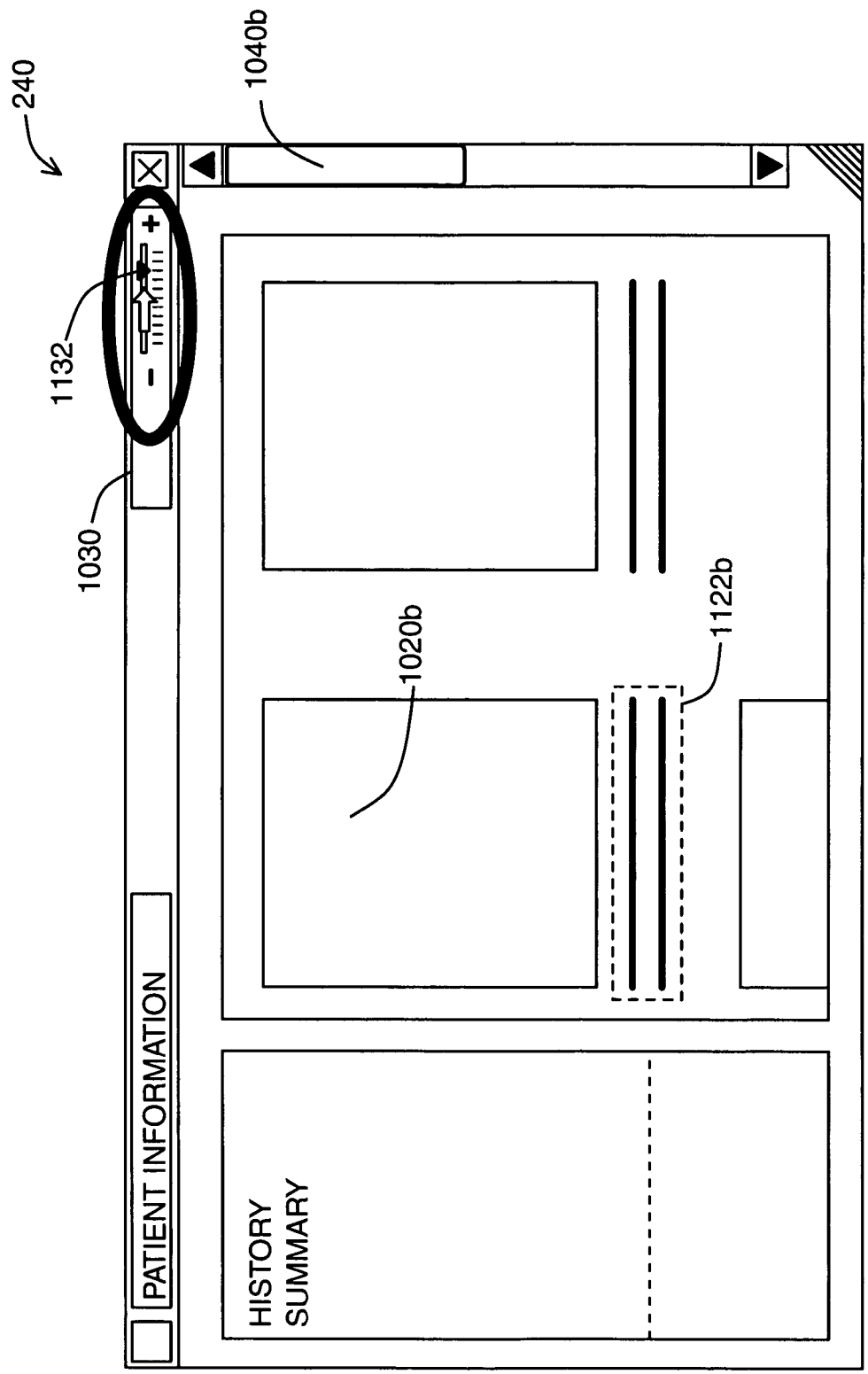
Figure 11:
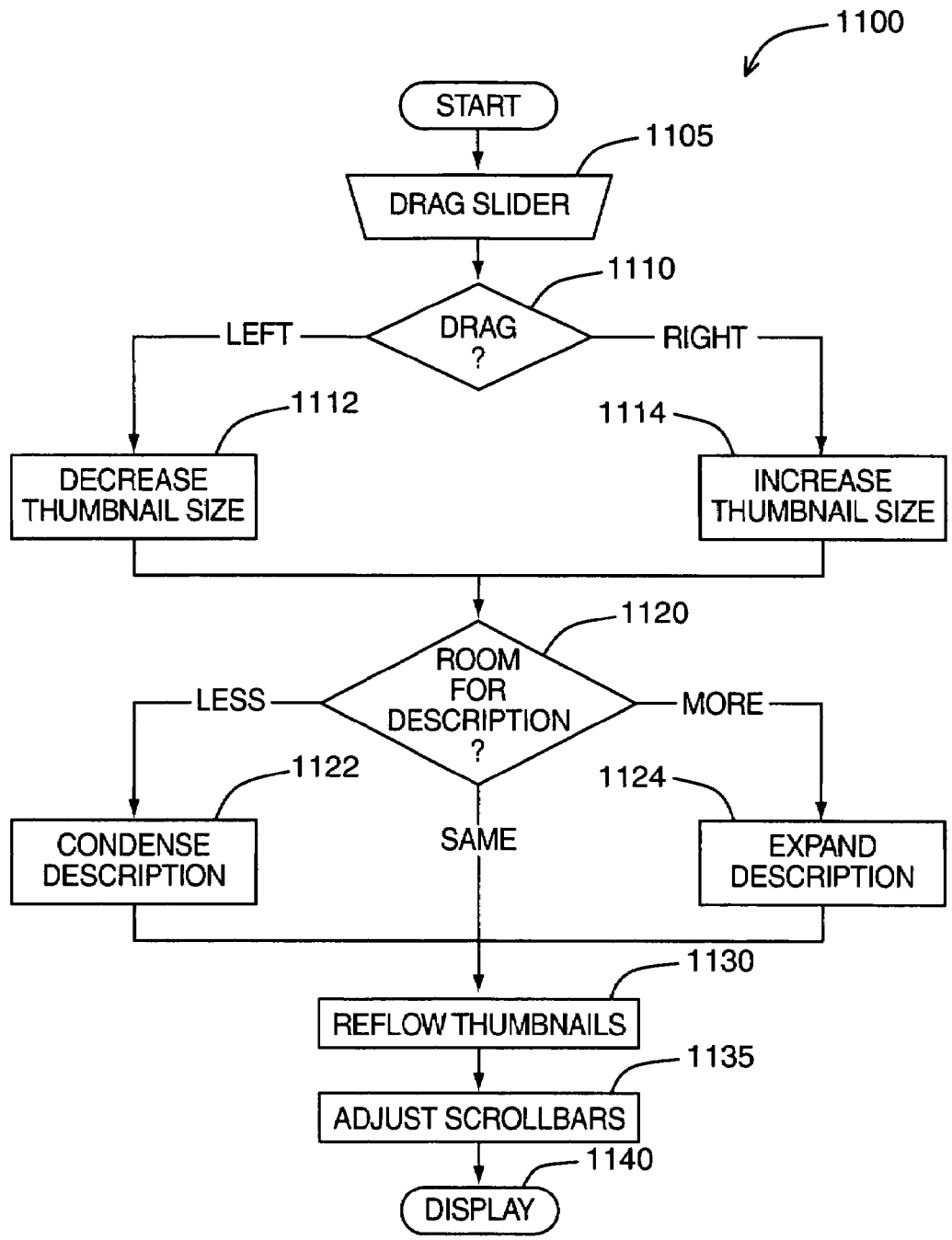
FIG. 11 is a flowchart diagram illustrating the operational steps executed by the imaging history display system performing the method of FIGS. 10A and 10B, according to the resize module of FIG. 1.

Referring now to FIGS. 10A, 10B and 11, there is shown a process for modifying the size of thumbnails 340 in imaging study list 142, using resize module 116. Reducing the size of thumbnails 340 (FIG. 10A) allows user 106 to perform gross comparisons quickly between large numbers of display entities 147. Conversely, increasing the size of thumbnails 340 (FIG. 10B) allows for more of text descriptions 350 to be displayed, enabling user 106 to see more information about each display entity 147 currently in view. The resize module 116 provides user 106 with the ability to quickly make gross comparisons to identify display entities 147 of interest and quickly identify specific display entities 147 based on their text descriptions 350, without necessitating the use of diagnostic interface 145.

FIG. 11 illustrates the process steps 1100 involved with changing the size of thumbnails 340. The resize module 116 is triggered by the user 106 through the selection and dragging of a resize slider 1030 from a position 1030 to a position 1032 at step (1105).

At step (1110), based on the relative coordinates of positions 1030 and 1032, resize module 116 determines if resize slider 1030 was dragged to the right, directing an increase in thumbnail size, or to the left, directing a decrease in thumbnail size. If resize slider 1030 was dragged to the right, resize module 116 increases the size of thumbnails 340 commensurate to the relative distance between positions 1030 and 1032 at step (1114). Conversely, if resize slider 1030 was dragged to the left, resize module 116 decreases the size of thumbnails 340 commensurate to the relative distance between positions 1030 and 1032 at step (1112).

Resize module 116 determines if text description 350, as currently formatted, will fit in the allotted text area 1122b beneath each thumbnail 340, at the new size, at step (1120). If the current format of text description 350 requires no change to fit in the allotted text area 1122b and no extra detail can be added, no change is made. If the current format of text description 350 is too large to fit in the allotted text area 1122*b*, resize module 116 condenses text description 350 for each thumbnail at step (1122), progressively trimming less relevant data in a preferred order. For example, resize module 116 eliminates the display of slice width, time, the word "images", in that order, and finally truncates the thumbnail name for each text description 350. If the current format of text description 350 is condensed and more space is available in allotted text area 1122*b*, resize module 116 expands text description 350 for each thumbnail at step (1124), progressively adding more relevant data in a preferred order. For example, resize module 116 adds the full name, the word "image", time and slice width, in that order, to each text description 350.

At step (1130), resize module 116 rearranges or "reflows" thumbnails 340 to accommodate their new size, while observing the display width limit by increasing the vertical size of imaging study list 142, pushing thumbnails 340 onto new lines, if necessary. At step (1135), resize module 116 determines if scroll bars 1040*a* or 1040*b* are required to scroll through study list 142 and enables or disables them as necessary. Finally, the new arrangement of imaging study list 142 is displayed at step (1140).

Figure 12B:
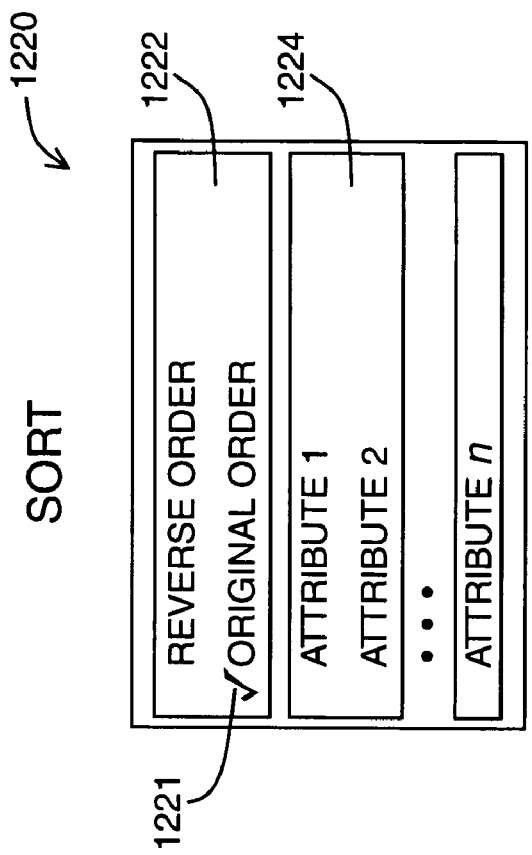
FIGS. 12A and 12B are schematic diagrams of two embodiments of the contextual toolset of FIG. 3.
Figure 12A:
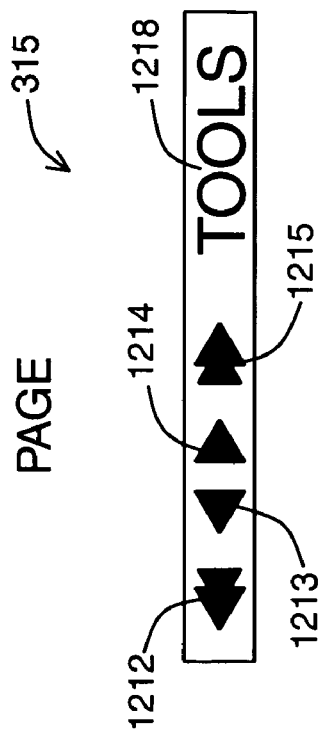

Referring now to FIG. 12A there is shown a schematic diagram of contextual toolbar 315. Contextual toolbar 315 is generated by paging module 119 for display in patient summary interface 140 for any medical imaging study view 250 that is linked with an imaging study 143 currently opened in diagnostic interface 145. Correspondingly, contextual toolbar 315 is available in docked patient summary interface modes 800*a* or 800*b*. Contextual toolbar 315 contains user interface elements to enable user 106 to incrementally view each imaging series 141 within the current medical imaging study view 250 in detail on diagnostic interface 145.

Specifically, contextual toolbar 315 contains: a backward double-arrow 1212, for paging backward through imaging series 141 in medical imaging study view 250 (e.g., selecting backward through the current study list 142 by a number equal to the amount of currently displayed imaging series 141, until the study list is exhausted); a backward single-arrow 1213, for selecting backward through imaging series 141 in medical imaging study view 250 one at a time; a forward single-arrow 1214, for selecting forward through imaging series 141 in medical imaging study view 250 one at a time; and a forward double-arrow 1215, for paging forward through imaging series 141 in medical imaging study view 250 (e.g., selecting forward through the current imaging study 143 by a number equal to the amount of currently displayed imaging series 141, to the end of all series for the study. Additionally, contextual toolbar 315 contains a tool menu disclosure command 1218 to invoke the display of a tool menu (not shown).

User 106 may also invoke a contextual tool menu 1220 by right-clicking any thumbnail, whereby sort module 122 generates and displays menu items based on relevant attributes of the currently displayed thumbnails. FIG. 12B illustrates one example embodiment of contextual tool menu 1220. For example, relevant attributes to display as menu items 1224 may be slice position, MR echo time, acquisition time, etc. Not all such attributes are relevant to all thumbnail (series), accordingly sort module 122 identifies relevant attributes based on a plurality of rules and dynamically generates the list of menu items 1224.

Additionally, sort module 122 always displays the menu items 1222, for specifying the sort ordering, either original or reverse. The current display order is indicated by an indicator checkmark 1221.

Figure 13:
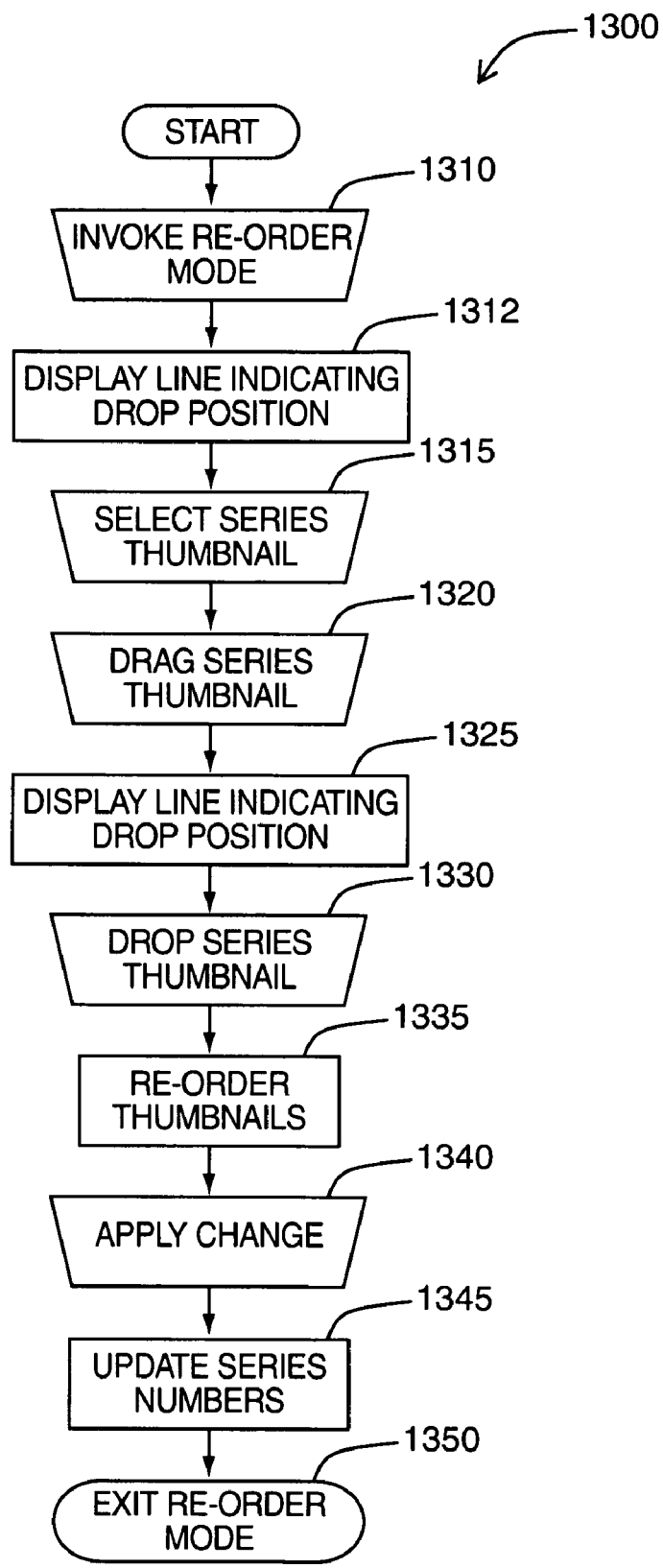
FIG. 13 is a flowchart diagram illustrating the operational steps executed by the imaging history display system of FIG. 2 performing the method of FIGS. 12C and 12D, according to the order module of FIG. 1.

Referring now to FIGS. 12C, 12D and 13, there is shown a process for reordering imaging series 141 in imaging study view 250 using order module 121. For certain modalities, for example angiography, it is common for series ordering and series descriptions to be incorrect. Alternatively, images in older imaging studies 141 may have been acquired in a random order, as they were scanned from film. Order module 121 allows user 106 to quickly correct inaccuracies in the order of imaging series 141 and retain changes for future sessions.

User 106 begins at step (1310) by invoking reorder mode from the list of options display when tool menu disclosure command 1218 is selected. Order module 121 provides a visual indication that reorder mode is active at step (1312), by altering the series outline 355 to incorporate a drop-down tab 1232 containing commands to apply order changes 1233*a* or cancel reorder mode 1233*b*. User 106 selects one or more series thumbnail 1240*a* to rearrange at step (1315) and begins dragging it at step (1320). As user 106 drags series thumbnail 1240*a*, order module 121 draws and redraws a gray line 1234 at step (1325) proposing a position that series thumbnail 1240*a* will take up upon immediate conclusion of the drag operation. When user 106 is satisfied with the proposed position, a mouse button (on, e.g., input device 154) is released at step (1330) to complete the drag operation.

Order module 121 then displays imaging series 141 in the newly-selected position. If user 106 is satisfied with the change, apply order changes 1233*a* command is clicked at step (1340). If user 106 is dissatisfied with the change, cancel reorder mode 1233*b* may be selected (step not shown) or a new drag operation may be initiated, as described above. If changes were made, order module 121 applies new numbers to each imaging series 141, to indicate the new order, at step (1345) and patient summary interface 140 returns to normal operation at step (1350). It should be understood that more than one series can be moved at a time by selecting multiple series and moving them together (e.g. using the "Shift-select" method to select consecutive series and the "Ctrl-select" method to select non-consecutive series).

Figure 14:
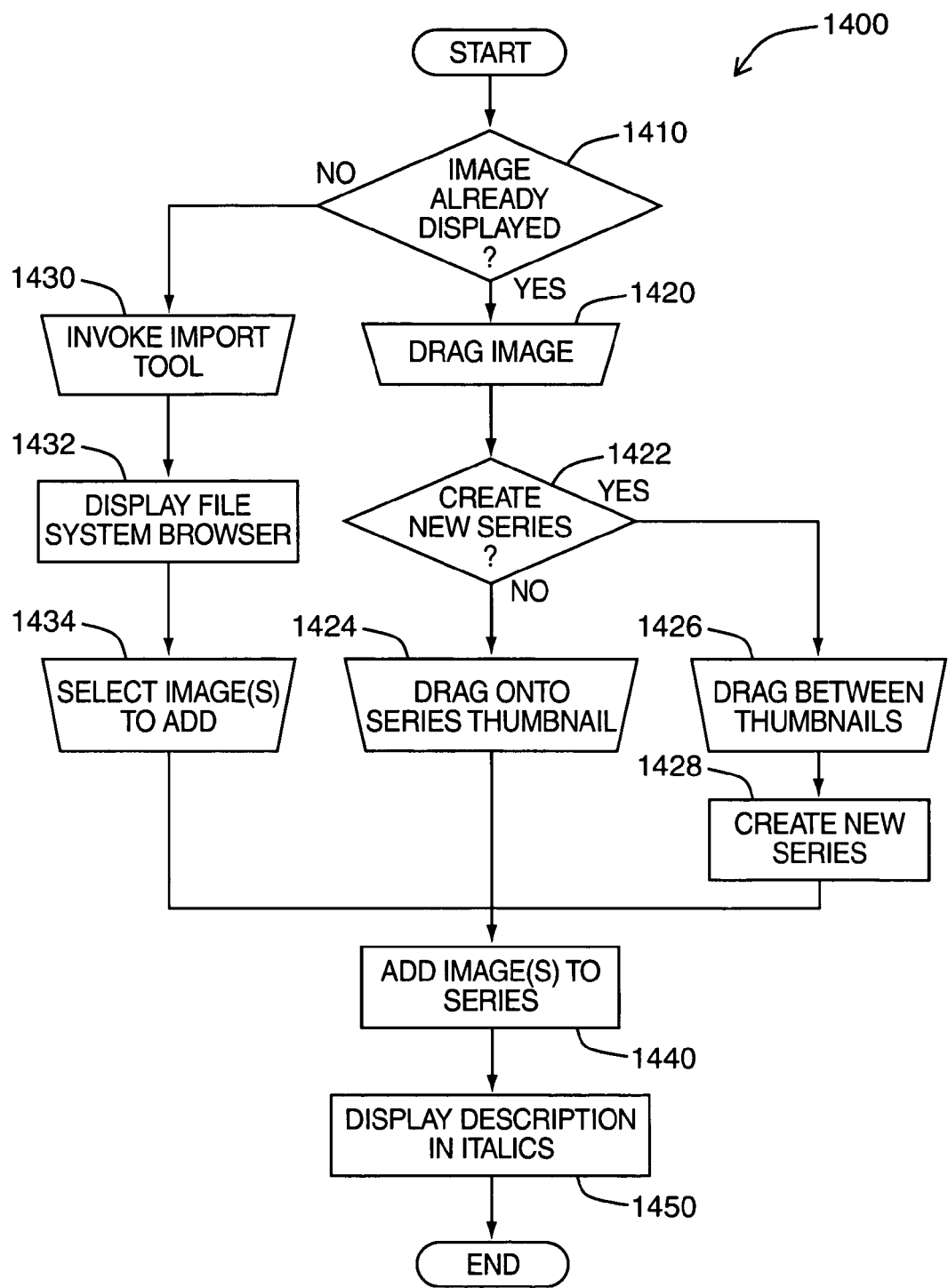
FIG. 14 is a flowchart diagram illustrating the operational steps executed by the imaging history display system of FIG. 2 according to the organization module of FIG. 1.

FIG. 14 is a flowchart diagram illustrating the operational steps 1400 taken by user 106, using add module 120, to add medical images to imaging study 141. The process begins at step (1410) by determining which method to follow, based on the display state of the image. If the image is already in view elsewhere, the user 106 drags the image onto medical imaging study view 250 at step (1420).

The user 106 then decides if a new series 290 is desired at step (1422). If yes, user 106 drags the image between two series thumbnails at step (1426), add module 120 creates a new series 290 to accept the image. If a new series is not desired, user 106 drags the image onto an existent series thumbnail at step (1424), whereby add module 120 determines that the image should be added to the selected series. If the image is not already in view elsewhere, user 106 must invoke the import tool item from the menu list obtained by issuing tool menu disclosure command 1218 at step (1430). Add module 120 displays a file system browser at step (1432) and user 106 selects an image at step (1434) to add to the currently selected series 290.

At step (1440), add module 120 adds the desired image to the series 290 identified as the target in the respective above branch followed. Add module 120 further alters the text description 350 of the modified series to display in italicized text, to indicate that it has been modified, at step (1450).

It should be understood that while the process steps 1400 are being described with respect to adding a single image, more than one image may be added concurrently using the same method.

User 106 uses organize module 123 to duplicate, combine or split imaging series 290 displayed in medical imaging study view 250. To employ any of the features of organize module 123, user 106 must first either select a series 290 in diagnostic interface 145 or select one or more series 290 in patient summary interface, before activating tool menu 1218. Upon activation of tool menu 1218, organize module 123 determines contextual menu (not shown) options to display, based on the display entities 147 currently selected.

The duplicate function of organize module 123 allows user 106 to create a temporary copy of an imaging series 290. This allows user 106 to easily compare window levels on a series with itself. For example, the imaging series can be displayed with a window level that highlights bone, while the duplicated imaging series can have a tissue window level applied. Series 290 may be duplicated by organize module 123 based on a user command, or in response to a drag operation dragging an already-open series from patient summary interface 140 into a supplemental viewing area of diagnostic interface 145.

The combine function of organize module 123 allows user 106 to temporarily combine imaging series 290 into a single series. This may be necessary for medical images originating from certain modalities 107, for example, CR and ultrasound.

Figure 15:
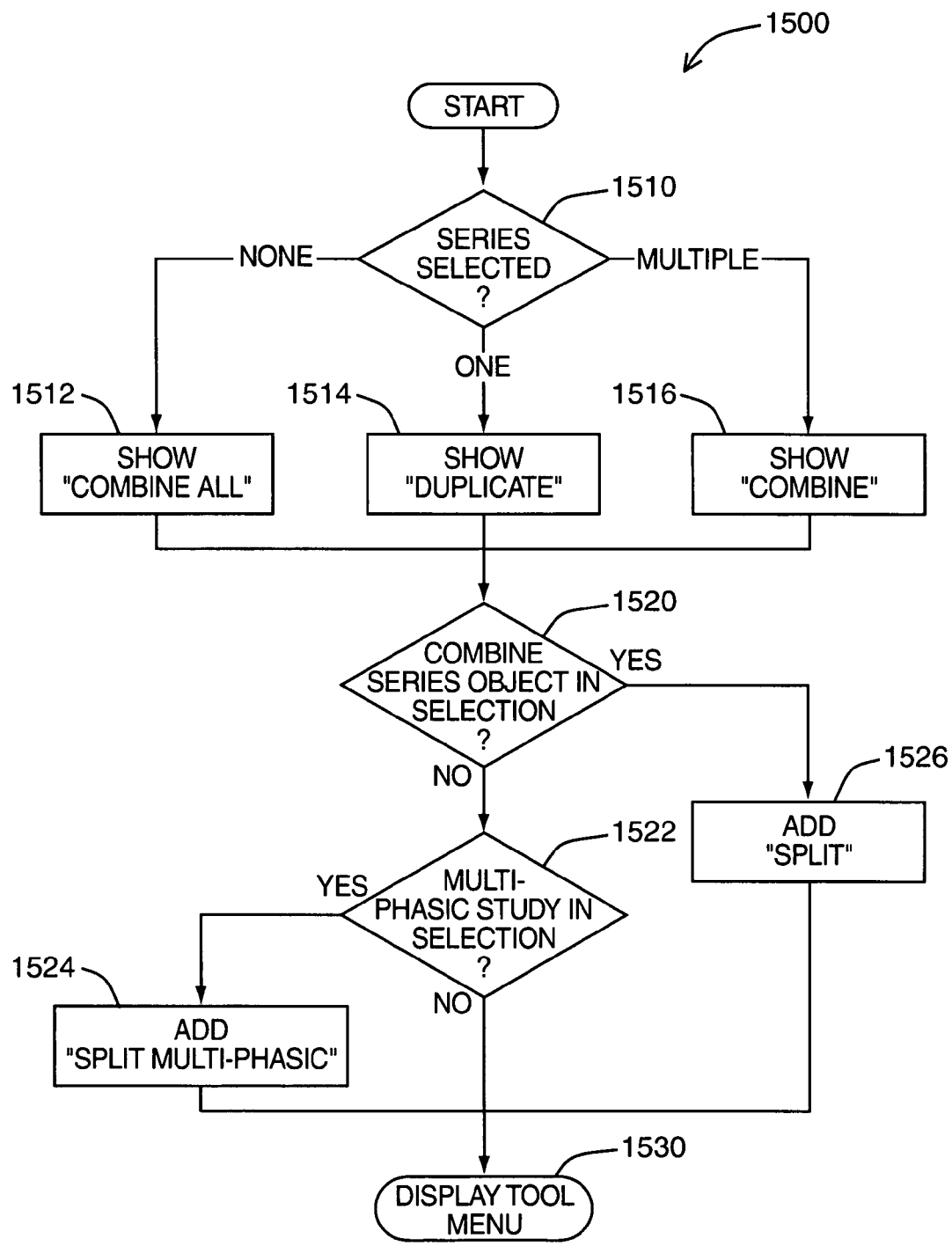
FIG. 15 is a flowchart diagram illustrating the operational steps executed by the imaging history display system of FIG. 2 determining the presentation of the contextual toolset module of FIG. 3.

Referring now to FIG. 15, there is shown a flowchart diagram illustrating the operational steps 1500 executed by organize module 123, to determine which command options to include in the contextual menu. Organize module 123 begins at step (1510) by identifying how many series 290 are currently selected. If there is no currently selected series 290, organize module 123 adds a "combine all" command to the menu list at step (1512). If there is only one currently selected series 290, organize module 123 adds a "duplicate" command to the menu list at step (1514). If there is more than one currently selected series 290, organize module 123 adds a "combine" command to the menu list at step (1516).

At step (1520), organize module 123 determines if there is a combined series in the current selection. Combined series are series 290 which have been logically grouped into a single, virtual series by user 106. If yes, organize module 123 adds a "split" command to the menu list at step (1526) and displays the tool menu at step (1530). If there is no currently selected combined series, organize module 123 determines if there is a multi-phasic study, in the current selection at step (1522). Multi-phasic studies are series 290 which contain more than one imaging "pass" or "phase", such as a multiple-pass CT scan. If yes, organize module 123 adds a "split multi-phasic" command to the menu list at step (1524). In either case, the tool menu is displayed at step (1530).

The operations of organize module 123 are manipulations that cannot be saved. Temporarily combined series are indicated by the word "Combined" in the text description 350, along with the series indices in brackets (e.g., [2,3]) to identify which series are combined. Temporary duplicate series are indicated by the word "Copy" in the text description 350, which is also presented in italicized form. However, manipulated series may be saved as a snapshot. Snapshots are described in greater detail below.

Figure 16:
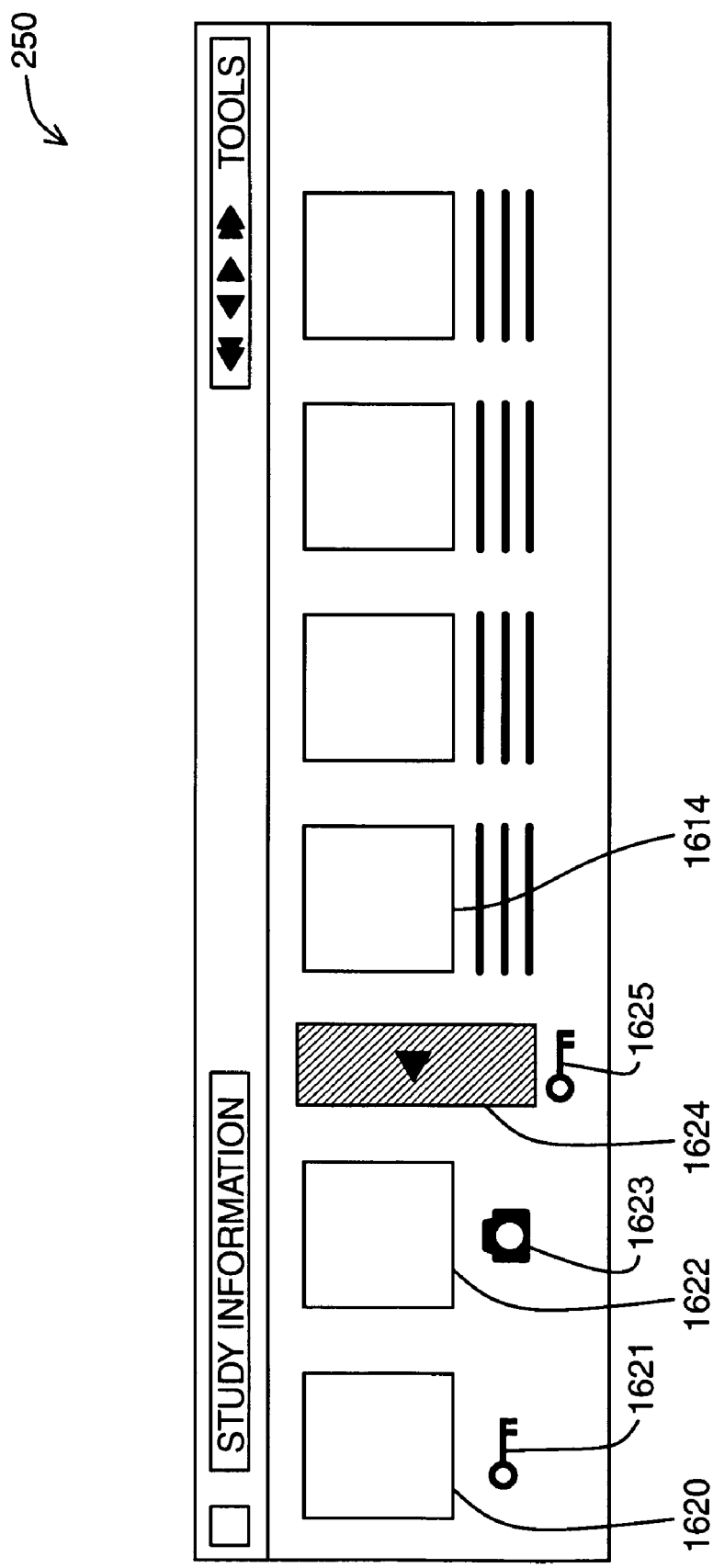
FIG. 16 is a schematic diagram of the interface of the image dataset series management tool of FIG. 3.

Referring now to FIG. 16, there is shown a medical imaging study view 250 with a key image 1620 and a snapshot image 1622, generated by the key image module 114. Key images 1620 and snapshot images 1622 may be established by the user 106 to facilitate later identification and comparison of a study 141 and are unique to each particular user 106, although all users can view other user's key images.

Key images 1620 and snapshot images 1622 are displayed first in each study 141 and indicated by a key icon 1621 and a camera icon 1623, respectively. Key images 1620 and snapshot images 1622 are further distinguished from other images in each study 141 through display of a divider bar 1624. User 106 may click divider bar 1624 to hide key images 1620 and snapshot images 1622 for each study 141. To redisplay key images 1620 and snapshot images 1622, user 106 right-clicks in an open space in medical imaging study view 250 and chooses a command option to display key images 1620 and snapshot images 1622. Key images have particular application for use with relevancy module 125, described in greater detail below with respect to FIGS. 17A and 17B.

The user 106 may elect to view key images 1620 and snapshot images 1622 selected by other users 106, by clicking an alternative key images command 1625. When alternative images 1625 are selected, key image module 114 displays a list of all key images 1620 and snapshot images 1622 created for the current study 141, along with the role and name of the user 106 who selected the images 1620 and 1622 and the number of highlighted images. By default, key image module 114 displays key images 1620 and snapshot images 1622 created by other users 106 in the same roles as the current user 106, including snapshots and key images created by the current user, if applicable. For example, for a radiologist user 106, key image module 114 will display images 1620 and 1622 created by other radiologists, and not surgical key images created by a neurosurgeon user 106.

The user 106 may also wish to review only imaging studies 141 of interest in patient summary interface 140. Therefore, imaging study view 250 allows user 106 to mark studies of interest and select a limited view mode, which hides unmarked studies. To redisplay all studies, user 106 issues a command to display all studies.

Figure 17B:
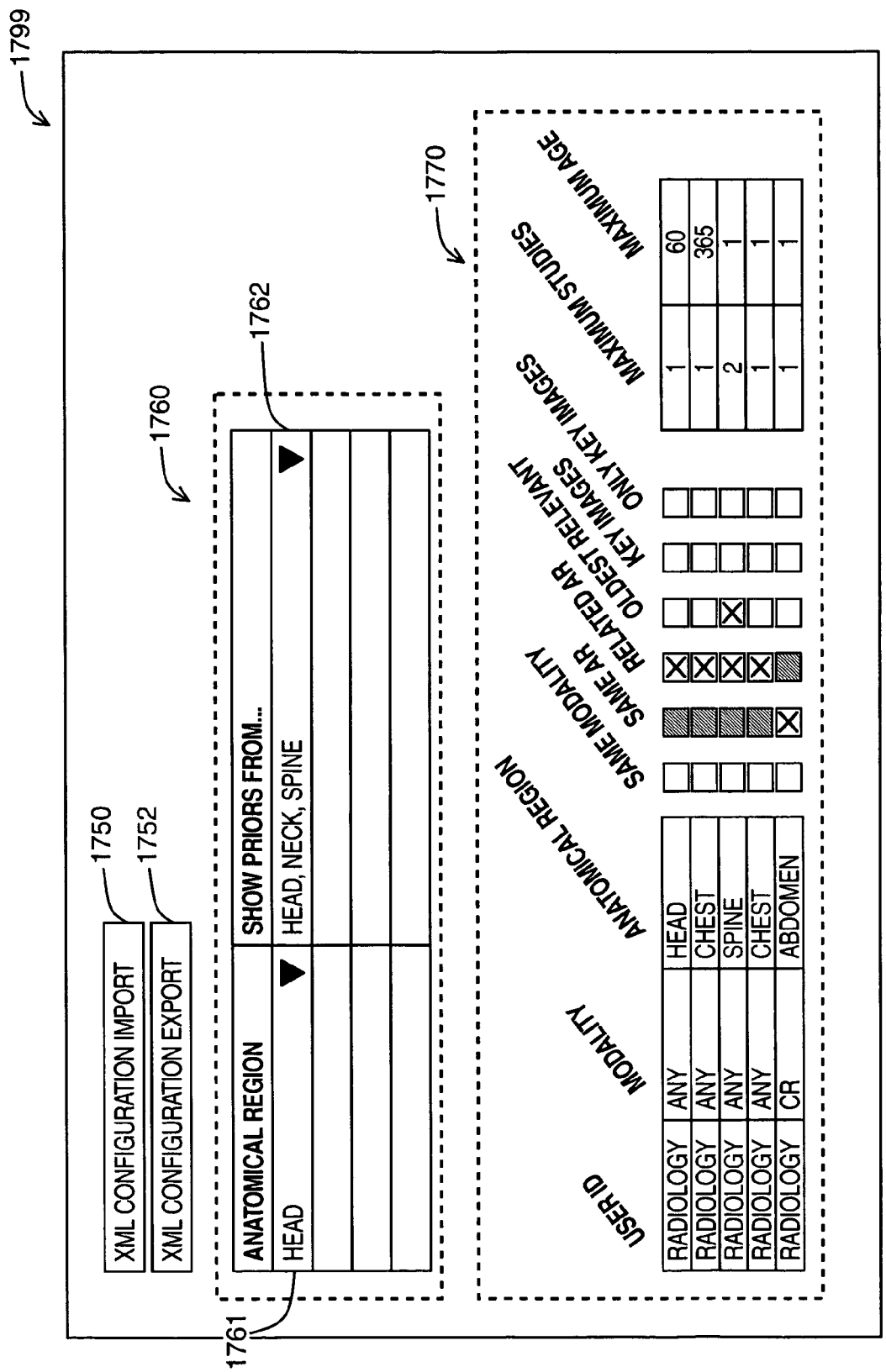

Referring now to FIGS. 17A and 17B, there are shown schematic diagrams of the relevancy mapping interface generated by relevancy module 125. Medical practitioner users 106 typically prefer to identify as many relevant prior studies as possible, to avoid missing any potentially important studies. For this reason, relevancy module 125 allows an administrative user 106a (not shown) to create or modify relevancy mappings between study description keywords or phrases and anatomic regions and then to create or modify relevancy mappings between anatomic regions, as will be described.

Referring first to FIG. 17A, the anatomic region mapping interface 1701 allows administrator 106a to create or modify mappings using a mappings table 1720. Each mapping rule contains a matching description 1724, which is used to identify a key word or phrase (i.e. "textual element") appearing in study descriptions. Matching description 1724 may contain wildcard characters (e.g. "%") to group sets of studies. If a study description contains the text specified in one of the matching descriptions 1724 in mappings table 1720, then the study will be mapped to the one or more anatomical regions listed in the associated association field 1726 by relevancy module 125.

Each mapping rule also contains an association field 1726 that comprises a list of one or more anatomical regions (e.g. "Head", "Neck", "Spine"). The administrator 106a can edit the association field 1726 to select or deselect existing anatomical regions listed therein and reduce or expand the definition of the association field 1726 to remove or include selected anatomical regions. Anatomical regions include, for example, the following: "Whole Body", "Head", "Neck", "Spine", "Chest", "Abdomen", "Pelvis", "Upper Extremities" and "Lower Extremities". It should be understood that these are only provided as examples and that various other anatomical regions could be utilized (e.g. "Hand to Shoulder", "Hip to Foot", etc.).

Mappings table 1720 allows administrator 106a to define new mapping rules using a new rule button 1730. Mappings may be imported in an extensible markup language (XML) format by clicking an XML import command 1710. Alternatively, mappings may be imported in a human-readable text description format, whereby each mapping is specified using one line of text (i.e., rules are delineated by a newline character), by clicking an import text descriptions command 1714. Correspondingly, mappings may be exported in XML or human-readable text formats by clicking XML export command 1712 or export text descriptions command 1716, respectively. Import and export of mappings between sites is desirable because it facilitates uniformity and predictability of results across systems. External systems may contain more detailed descriptions and mappings. If data is imported that conflicts with existing data, administrator 106a is given the option of replacing or appending mappings to the existing table of mappings.

Referring now to FIG. 17B, once studies have been mapped to specific anatomical regions, the imaging history display system 100 then allows the administrator 106a to define relevancy relationships among anatomical regions using an anatomic region relevancy interface 1799. For example, user 106 may wish to see prior pelvic studies when reviewing an abdominal study, but not all abdominal studies will be inherently mapped to the pelvic region. Anatomic region relevancy interface 1799 allows administrator 106a to specifically define broad relevancy criteria, along with preferred relevancy rankings for each anatomical region.

For example, "Head" studies are related to "Neck" and "Spine" studies but, when reviewing a "Head" study, users 106 will prefer to see prior "Head" studies first, followed by "Neck" studies and "Spine" studies, in that order. By defining these criteria using anatomic region relevancy interface 1799 (specific example illustrated in FIG. 17B), the relevancy module 125 will ensure that prior studies are presented to the user 106 in the preferred order. The relevancy module 125 will also ensure that each study is displayed only once in a list of relevant prior studies, in the case that a study matches more than one mapping. That is, if a study falls into multiple anatomical regions, it would only show up in the first available group in the list.

Using anatomic region relevancy interface 1799, the administrator 106a may import rules from an XML file using XML import command 1750. Correspondingly, rules may be exported using XML export command 1752. Administrator 106a may also manually specify rules using relevancy table 1760. Each row of relevancy table 1760 contains an anatomical region identifier 1761, specifying to which anatomical region the rule applies, and a relevancy ranking field 1762, which specifies associated relevant anatomical regions and the preferred order of relevancy. The administrator 106a may modify the list to add or delete anatomic regions, or change relevancy order.

Once studies have been classified in respect of anatomical regions as discussed above in relation to FIG. 17A, when a user 106 opens a study for review, the relevancy module 125 will examine the classification of the study and attempt to open all relevant prior studies that match the relevancy rules specified in table 1760. In some cases, this may create the problem of displaying too much information.

Therefore, the administrator 106a can specify constraints on relevant prior studies, using the constraints table 1770, which must be met in order for prior studies to be automatically opened. Rules in constraints table 1770 are specified by user identification, modality and anatomical region and may include: a "Same Modality" checkbox, to select only prior studies originating from the same modality; a "Same Anatomical Region" checkbox, to select only prior studies on the same anatomical region (note that when this checkbox is selected, the related anatomical region checkbox is unavailable); a "Related Anatomical Region" checkbox, to select only prior studies on a related anatomical region (note that when this checkbox is selected, the same anatomical region checkbox is unavailable); an "Oldest Relevant" checkbox, to select only the oldest relevant prior study; a "Key Image" checkbox, to select only prior studies that have key images; a "Show Key Images Only" checkbox, to only open key images from a selected prior study; a "Maximum Studies Limit", to specify the maximum number of relevant prior studies to open; and a "Maximum Age" limit, to specify the maximum age of a prior study to open.

In some cases, images from multiple modalities may be displayed within imaging history summary interface 240 (FIG. 6) that are not of the same anatomical region, and thus have conflicting relevancy relationships. To resolve relevancy conflicts and determine a list of relevant prior imaging studies 141 for display when the user 106 selects the "Show relevant" (or in the case of default operation), the relevancy module 125 uses a plurality of rules.

For example, all prior imaging studies 141 that have yet to be reported (e.g. are "to be dictated") are displayed first within the imaging history summary interface 240 (FIG. 6), regardless of relevancy conflict.

Also, the very first imaging study 141 displayed within the imaging history summary interface 240, determines the relevant prior imaging studies to be displayed. For example, if a "CT Chest" imaging study is the "newest" study for a "Chest/Abdomen/Pelvis" combination of imaging studies to be dictated then all relevant prior imaging studies for the "CT Chest" are displayed within the diagnostic interface 145 and the imaging history summary interface 240 is updated accordingly.

Subsequent unreported (i.e. undictated) imaging studies 141, which may not have all relevant prior imaging studies displayed, have a "View relevants" tool, located beside reporting tool 312 (FIG. 3) to force the display of relevant prior imaging studies, in lieu of the first set. If user 106 selects the "View relevants" tool for a particular unreported imaging study, the relevant prior imaging studies displayed within diagnostic interface 145 and imaging history summary interface 240 change to reflect the newly-selected study. Also, the "View relevants" tool appears for the former first imaging (or primary) study, and the "View relevants" tool disappears for the newly-selected study, to indicate that it is now the first imaging (or primary) study. When "show relevants" is selected, only relevant imaging studies 143 are displayed in both the imaging history summary 240 and the study list 142. Also, the color of all of the "open control buttons" will match the color of the study icons used.

It will be appreciated that while imaging history display system 100 has been described in the context of medical image management in order to provide an application-specific illustration, it should be understood that imaging history display system 100 could also be applied to any other type of image or document display system. The system, processes and methods described are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of providing a contextual historical summary display within a viewable area on a patient summary interface display of a computer terminal for a plurality of images wherein each image is associated with a date and adapted to be displayed on a diagnostic interface display of the computer terminal, said method comprising:
   (a) sorting the plurality of images using a processor into one or more image groups according to date and associating a representative icon with each image group;
   (b) initially grouping using the processor one or more representative icons together according to a first selection of time periods;
   (c) determining using the processor whether all of the representative icons will fit within the viewable area of the patient summary interface display when grouped according to the first selection of time periods;
   (d) if (c) is true then displaying the representative icons within the viewable area of the patient summary interface display according to the grouping in (b); and
   (e) if (c) is false then further grouping using the processor the representative icons according to a second selection of time periods and displaying the representative icons within the viewable area of the patient summary interface display, wherein at least one of the time periods in the second selection is comprised of two or more time periods from the first selection.

2. The method of claim 1, wherein the time period is selected from the group consisting of: month, year, and multi-month.

3. The method of claim 1, wherein for a current year, the initial grouping of representative icons in (b) is performed by grouping all representative icons associated with the same month for the current year and grouping all representative icons associated with the same year before the current year.

4. The method of claim 1, wherein the further grouping of representative icons in (e) is performed by grouping all representative icons associated with the same multi-month time period for the current year such that the representative icons associated with the same month are arranged on separate lines and grouping all representative icons associated with the same year before the current year.

5. The method of claim 1, wherein the further grouping of representative icons in (e) is performed by grouping all representative icons associated with the same multi-month time period for the current year such that the representative icons associated with the same month are arranged sequentially on each line and grouping all representative icons associated with the same year before the current year.

6. The method of claim 1, wherein the multi-month time period is a quarter.

7. The method of claim 1, wherein the further grouping of one or more representative icons is performed first on the representative icons associated with the oldest time periods.

8. The method of claim 1, wherein the representative icons are shown in reverse time period order.

9. The method of claim 1, wherein when a first image associated with a first representative icon is displayed on the diagnostic interface, the method further comprises associating a visual indication with the first representative icon within the history summary interface to indicate that the first image is being displayed.

10. The method of claim 1, wherein a plurality of legend icons are provided within the patient summary interface where a first legend icon is associated with a first legend color identifier and a first image characteristic and wherein a first representative icon is associated with a first representative color identifier and a second image characteristic such that when the first and second image characteristic are the same, the first legend color identifier and the first representative color identifier are the same.

11. The method of claim 1, wherein each image is associated with an imaging characteristic and wherein the method further comprises determining the relevancy of each of the images based on the imaging characteristic.

12. The method of claim 11, wherein the imaging characteristic is selected from the group consisting of a body part and a modality.

13. A computer-readable medium upon which a plurality of instructions are stored, the instructions for performing the steps of the method as claimed in claim 1.

14. A system for providing a contextual historical summary display within a viewable area on a patient summary interface display of a computer terminal for a plurality of images wherein each image is associated with a date and adapted to be displayed on a diagnostic interface display of the computer terminal, said system comprising:
   (a) a memory for storing the plurality of images; and
   (b) a processor coupled to the memory and for:
      (A) sorting the plurality of images into one or more image groups according to date and associating a representative icon with each image group;
      (B) initially grouping one or more representative icons together according to a first selection of time periods;
      (C) determining whether all of the representative icons will fit within the viewable area of the patient summary interface display when grouped according to the first selection of time periods;
      (D) determining if (C) is true, and if so then displaying the representative icons within the viewable area of the patient summary interface display according to the grouping in (B); and
      (E) determining if (C) is false, and if so then further grouping the representative icons according to a second selection of time periods and displaying the representative icons within the viewable area of the patient summary interface display, wherein at least one of the time periods in the second selection is comprised of two or more time periods from the first selection.

15. The system of claim 14, wherein the time period is selected from the group consisting of: month, year, and multi-month.

16. The system of claim 14, wherein for a current year, the initial grouping of representative icons in (B) is performed by grouping all representative icons associated with the same month for the current year and grouping all representative icons associated with the same year before the current year.

17. The system of claim 14, wherein the further grouping of representative icons in (E) is performed by grouping all representative icons associated with the same multi-month time period for the current year such that the representative icons associated with the same month are arranged on separate lines and grouping all representative icons associated with the same year before the current year.

18. The system of claim 14, wherein the further grouping of representative icons in (E) is performed by grouping all representative icons associated with the same multi-month time period for the current year such that the representative icons associated with the same month are arranged sequentially on each line and grouping all representative icons associated with the same year before the current year.

19. The system of claim 14, wherein the multi-month time period is a quarter.

20. The system of claim 14, wherein the further grouping of one or more representative icons is performed first on the representative icons associated with the oldest time periods.

21. The system of claim 14, wherein the representative icons are shown in reverse time period order.

22. The system of claim 14, wherein when a first image associated with a first representative icon is displayed on the diagnostic interface, the processor is further adapted to associate a visual indication with the first representative icon within the history summary interface to indicate that the first image is being displayed.

23. The system of claim 14, wherein a plurality of legend icons are provided within the patient summary interface where a first legend icon is associated with a first legend color identifier and a first image characteristic and wherein a first representative icon is associated with a first representative color identifier and a second image characteristic such that when the first and second image characteristic are the same, the first legend color identifier and the first representative color identifier are the same.

24. The system of claim 14, wherein each image is associated with an imaging characteristic and wherein the method further comprises determining the relevancy of each of the images based on the imaging characteristic.

25. The system of claim 24, wherein the imaging characteristic is selected from the group consisting of: a body part and a modality.

26. A method of associating a first image corresponding to a first anatomic region with a second image corresponding to a second anatomic region in a display terminal, said method comprising:
   (a) receiving via a relevancy mapping interface a first anatomical mapping for the first image to associate it with the first anatomic region, and storing the first anatomical mapping in a memory;
   (b) receiving via the relevancy mapping interface a second anatomical mapping for the second image to associate it with the second anatomic region, and storing the second anatomical mapping in the memory;
   (c) receiving via an anatomic region relevancy mapping interface an anatomical relevancy rule that maps the first anatomic region to at least one anatomic region including the second anatomic region, and storing the anatomical relevancy rule in the memory;
   (d) applying the anatomical relevancy rule to the first image using a processor to determine whether the first anatomic region is mapped to the second anatomic region; and
   (e) if (d) is true then associating the first image with the second image in the memory and displaying the second image on a computer display in association with the first image.

27. The method of claim 26, wherein the first anatomical mapping contains a first textual element and the second anatomical mapping contains a second textual element.

28. The method of claim 26, wherein the first and second images include at least one image characteristic and the application of the anatomic relevancy rule is limited according to whether at least one of the image characteristics associated with the first and second images match.

29. A computer-readable medium upon which a plurality of instructions are stored, the instructions for performing the steps of the method as claimed in claim 26.

30. A display terminal system for associating a first image corresponding to a first anatomic region with a second image corresponding to a second anatomic region, said system comprising:
   (a) a memory for storing the first and second images;
   (b) a processor coupled to the memory for:
      (A) receiving via a relevancy mapping interface a first anatomical mapping for the first image to associate it with the first anatomic region, and storing the first anatomical mapping in the memory;
      (B) receiving via a relevancy mapping interface a second anatomical mapping for the second image to associate it with the second anatomic region, and storing the second anatomical mapping in the memory;
      (C) receiving via an anatomic region relevancy mapping interface an anatomical relevancy rule that maps the first anatomic region to at least one anatomic region including the second anatomic region, and storing the anatomical relevancy rule in the memory;
      (D) applying the anatomical relevancy rule to the first image to determine whether the first anatomic region is mapped to the second anatomic region; and
      (E) if (D) is true then associating the first image with the second image in the memory and displaying the second image on a computer display in association with the first image.

31. The system of claim 30, wherein the first anatomical mapping contains a first textual element and the second anatomical mapping contains a second textual element.

32. The system of claim 30, wherein the first and second images include at least one image characteristic and the application of the anatomic relevancy rule is limited according to whether at least one of the image characteristics associated with the first and second images match.

* * * * *